United States Patent
Kang et al.

(10) Patent No.: US 11,807,683 B2
(45) Date of Patent: Nov. 7, 2023

(54) ANTIBODY BINDING TIM-3 AND USE THEREOF

(71) Applicant: Nanjing Leads Biolabs Co., Ltd., Jiangsu (CN)

(72) Inventors: Xiaoqiang Kang, Plainsboro, NJ (US); Shoupeng Lai, Germantown, MD (US); Xiao Huang, Jiangsu (CN)

(73) Assignee: Nanjing Leads Biolabs Co., Ltd., Nanjing (CN)

( * ) Notice: Subject to any disclaimer, the term of this patent is extended or adjusted under 35 U.S.C. 154(b) by 259 days.

(21) Appl. No.: 17/046,388

(22) PCT Filed: Apr. 11, 2019

(86) PCT No.: PCT/CN2019/082318
§ 371 (c)(1),
(2) Date: Oct. 9, 2020

(87) PCT Pub. No.: WO2019/196911
PCT Pub. Date: Oct. 17, 2019

(65) Prior Publication Data
US 2021/0221885 A1    Jul. 22, 2021

Related U.S. Application Data

(60) Provisional application No. 62/656,358, filed on Apr. 12, 2018.

(51) Int. Cl.
*A61K 39/395* (2006.01)
*C07K 16/28* (2006.01)
(Continued)

(52) U.S. Cl.
CPC .... *C07K 16/2803* (2013.01); *A61K 39/39541* (2013.01); *A61K 38/2013* (2013.01);
(Continued)

(58) Field of Classification Search
None
See application file for complete search history.

(56) References Cited

U.S. PATENT DOCUMENTS

2015/0218274 A1    8/2015   Sabatos-Peyton et al.
2016/0200815 A1    7/2016   Feldman et al.
(Continued)

FOREIGN PATENT DOCUMENTS

CN    103079644 A    5/2013
CN    107405397      11/2017
(Continued)

OTHER PUBLICATIONS

AcroBiosystems, cat# TM3-H5229, Retrieved online:<URL:https://www.acrobiosystems.com/P737-Human-TIM-3--HAVCR2-Protein-His-Tag-%28MALS-verified%29.html>. [Retrieved Dec. 27, 2022] 2022.*
(Continued)

*Primary Examiner* — Claire Kaufman
(74) *Attorney, Agent, or Firm* — Wolf, Greenfield & Sacks, P.C.

(57) ABSTRACT

The present invention provides an isolated monoclonal antibody that specifically binds human TIM-3. The present invention further provides a pharmaceutical composition comprising the antibody, as well as uses thereof.

23 Claims, 4 Drawing Sheets

Specification includes a Sequence Listing.

(51) Int. Cl.
    *A61K 38/20*     (2006.01)
    *A61K 39/00*     (2006.01)

(52) U.S. Cl.
    CPC .... *A61K 2039/505* (2013.01); *C07K 16/2818* (2013.01); *C07K 16/2827* (2013.01); *C07K 16/2878* (2013.01); *C07K 2317/24* (2013.01); *C07K 2317/76* (2013.01)

(56) References Cited

U.S. PATENT DOCUMENTS

2017/0190777 A1   7/2017   Sabatos-Peyton et al.
2017/0240633 A1   8/2017   Wang et al.

FOREIGN PATENT DOCUMENTS

| CN | 107922484 | 4/2018 |
| IN | 201617029582 | 1/2017 |
| TW | 201736397 A | 10/2017 |
| WO | WO 2016161270 A1 | 10/2016 |
| WO | WO 2017031242 A1 | 2/2017 |
| WO | WO 2017079115 A1 | 5/2017 |
| WO | WO 2017205721 A1 | 11/2017 |
| WO | WO 2018013818 A2 | 1/2018 |
| WO | WO 2018036561 A1 | 3/2018 |
| WO | WO 2018039020 A1 | 3/2018 |

OTHER PUBLICATIONS

Yan et al., Construction of a synthetic phage-displayed Nanobody library with CDR3 regions randomized by trinucleotide cassettes for diagnostic applications, J. Translational Med. 12:343, 12 pages, 2014.*

Kranz et al., Restricted reassociation of heavy and light chains from hapten-specific monoclonal antibodies, Proc. Natl. Acad. Sci. USA, 78(9):5807-5811, Sep. 1981.*

Banerjee et al., Immune regulation by Tim-3 [version 1; peer review: 2 approved]. F1000Research (F1000 Faculty Rev):316, 9 pages, (https://doi.org/10.12688/f1000research.13446.1), Mar. 31, 2018.*

International Search Report dated Jul. 30, 2019 in connection with International Application No. PCT/CN2019/082318.

Gao et al., TIM-3 expression characterizes regulatory T cells in tumor tissues and is associated with lung cancer progression. PLOS One. 2012;7(2):e30676. doi: 10.1371/journal.pone.0030676. Epub Feb. 17, 2012.

Gleason et al., Tim-3 is an inducible human natural killer cell receptor that enhances interferon gamma production in response to galectin-9. Blood. Mar. 29, 2012;119(13):3064-72. doi: 10.1182/blood-2011-06-360321. Epub Feb. 8, 2012.

Hastings et al., TIM-3 is expressed on activated human CD4+ T cells and regulates Th1 and Th17 cytokines. Eur J Immunol. Sep. 2009;39(9):2492-501. doi: 10.1002/eji.200939274.

Monney et al., Th1-specific cell surface protein Tim-3 regulates macrophage activation and severity of an autoimmune disease. Nature. Jan. 31, 2002;415(6871):536-41. doi: 10.1038/415536a.

Ngiow et al., Anti-TIM3 antibody promotes T cell IFN-γ-mediated antitumor immunity and suppresses established tumors. Cancer Res. May 15, 2011;71(10):3540-51. doi: 10.1158/0008-5472.CAN-11-0096. Epub Mar. 23, 2011.

Ngiow et al., Prospects for TIM3-Targeted Antitumor Immunotherapy. Cancer Res. Nov. 1, 2011;71(21):6567-71. doi: 10.1158/0008-5472. CAN-11-1487. Epub Oct. 18, 2011.

Sabatos-Peyton et al., Blockade of Tim-3 binding to phosphatidylserine and CEACAM1 is a shared feature of anti-Tim-3 antibodies that have functional efficacy. Oncoimmunology. Nov. 9, 2017;7(2):e1385690. doi: 10.1080/2162402X.2017.1385690.

Sabatos et al., Interaction of Tim-3 and Tim-3 ligand regulates T helper type 1 responses and induction of peripheral tolerance. Nat Immunol. Nov. 2003;4(11):1102-10. doi: 10.1038/ni988. Epub Oct. 12, 2003.

* cited by examiner

SEQUENCE LISTING

<160> NUMBER OF SEQ ID NOS: 57

<210> SEQ ID NO 1
<211> LENGTH: 5
<212> TYPE: PRT
<213> ORGANISM: Artificial Sequence
<220> FEATURE:
<223> OTHER INFORMATION: Synthetic

<400> SEQUENCE: 1

Ser Tyr Thr Ile Ser
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic

<400> SEQUENCE: 2

Ser Tyr Thr Ile Tyr
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic

<400> SEQUENCE: 3

Ser Tyr Ala Met Ser
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic

<400> SEQUENCE: 4

Ser Asn Ser Ala Ala Trp Asn
1               5

<210> SEQ ID NO 5

```
<211> LENGTH: 17
<212> TYPE: PRT
<213> ORGANISM: Artificial Sequence
<220> FEATURE:
<223> OTHER INFORMATION: Synthetic

<400> SEQUENCE: 5

Arg Ile Ile Pro Ile Leu Gly Thr Ala Asn Tyr Ala Gln Lys Phe Gln
1               5                   10                  15

Gly

<210> SEQ ID NO 6
<211> LENGTH: 17
<212> TYPE: PRT
<213> ORGANISM: Artificial Sequence
<220> FEATURE:
<223> OTHER INFORMATION: Synthetic

<400> SEQUENCE: 6

Ser Ile Ile Pro Ile Leu Gly Thr Ala Asn Tyr Ala Gln Lys Phe Gln
1               5                   10                  15

Gly

<210> SEQ ID NO 7
<211> LENGTH: 17
<212> TYPE: PRT
<213> ORGANISM: Artificial Sequence
<220> FEATURE:
<223> OTHER INFORMATION: Synthetic

<400> SEQUENCE: 7

Gly Ile Ser Gly Ser Gly Gly Ser Thr Tyr Tyr Ala Asp Ser Val Lys
1               5                   10                  15

Gly

<210> SEQ ID NO 8
<211> LENGTH: 18
<212> TYPE: PRT
<213> ORGANISM: Artificial Sequence
<220> FEATURE:
<223> OTHER INFORMATION: Synthetic

<400> SEQUENCE: 8

Arg Thr Tyr Tyr Arg Ser Lys Trp Tyr Asn Asp Tyr Ala Val Ser Val
1               5                   10                  15

Lys Ser

<210> SEQ ID NO 9
<211> LENGTH: 5
<212> TYPE: PRT
<213> ORGANISM: Artificial Sequence
<220> FEATURE:
<223> OTHER INFORMATION: Synthetic

<400> SEQUENCE: 9

Ala Ser His Thr Ile
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic
```

```
<400> SEQUENCE: 10

Ser Tyr Tyr Asp Asp Ala Phe Asp Ile
1               5

<210> SEQ ID NO 11
<211> LENGTH: 16
<212> TYPE: PRT
<213> ORGANISM: Artificial Sequence
<220> FEATURE:
<223> OTHER INFORMATION: Synthetic

<400> SEQUENCE: 11

Asp Gln Ala Ala Gly Phe Pro Gln Pro Tyr Ile Tyr Gly Met Asp Val
1               5                   10                  15

<210> SEQ ID NO 12
<211> LENGTH: 14
<212> TYPE: PRT
<213> ORGANISM: Artificial Sequence
<220> FEATURE:
<223> OTHER INFORMATION: Synthetic

<400> SEQUENCE: 12

Ala Ser Ser Thr Gly Ala Val Thr Ser Gly Tyr Ser Pro Asn
1               5                   10

<210> SEQ ID NO 13
<211> LENGTH: 14
<212> TYPE: PRT
<213> ORGANISM: Artificial Sequence
<220> FEATURE:
<223> OTHER INFORMATION: Synthetic

<400> SEQUENCE: 13

Ala Ser Ser Thr Gly Ala Val Thr Ser Gly Asn Thr Pro Asn
1               5                   10

<210> SEQ ID NO 14
<211> LENGTH: 14
<212> TYPE: PRT
<213> ORGANISM: Artificial Sequence
<220> FEATURE:
<223> OTHER INFORMATION: Synthetic

<400> SEQUENCE: 14

Ala Ser Ser Thr Gly Ala Val Thr Ser Gly Tyr Thr Pro Asn
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Synthetic

<400> SEQUENCE: 15

Arg Ala Ser Gln Ser Val Thr Lys Asp Leu Val Ala
1               5                   10

<210> SEQ ID NO 16
<211> LENGTH: 13
<212> TYPE: PRT
<213> ORGANISM: Artificial Sequence
<220> FEATURE:
<223> OTHER INFORMATION: Synthetic

<400> SEQUENCE: 16
```

Thr Gly Asn Ser Asn Asn Val Gly Asn Gln Gly Ala Ala
1               5                   10

<210> SEQ ID NO 17
<211> LENGTH: 7
<212> TYPE: PRT
<213> ORGANISM: Artificial Sequence
<220> FEATURE:
<223> OTHER INFORMATION: Synthetic

<400> SEQUENCE: 17

Thr Thr Ser Asn Arg His Ser
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic

<400> SEQUENCE: 18

Thr Thr Asn Asn Arg His Ser
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic

<400> SEQUENCE: 19

Gly Ala Ser Ser Arg Ala Thr
1               5

<210> SEQ ID NO 20
<211> LENGTH: 7
<212> TYPE: PRT
<213> ORGANISM: Artificial Sequence
<220> FEATURE:
<223> OTHER INFORMATION: Synthetic

<400> SEQUENCE: 20

Arg Thr Asn Asn Arg Pro Ser
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic

<400> SEQUENCE: 21

Leu Leu Tyr Tyr Gly Gly Ala Trp Val
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic

<400> SEQUENCE: 22

Gln Gln Tyr Gly Arg Ser Pro Leu Thr
1               5

<210> SEQ ID NO 23
<211> LENGTH: 11
<212> TYPE: PRT
<213> ORGANISM: Artificial Sequence
<220> FEATURE:
<223> OTHER INFORMATION: Synthetic

<400> SEQUENCE: 23

Ser Gly Trp Asp Ser Ser Leu Asn Glu Gly Val
1               5                   10

<210> SEQ ID NO 24
<211> LENGTH: 114
<212> TYPE: PRT
<213> ORGANISM: Artificial Sequence
<220> FEATURE:
<223> OTHER INFORMATION: Synthetic

<400> SEQUENCE: 24

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Thr Ile Ser Trp Val Arg Gln Ala Pro Gly Gln Gly Leu Glu Trp Met
        35                  40                  45

Gly Arg Ile Ile Pro Ile Leu Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Ala Ser His Thr Ile Trp Gly Lys Gly Thr Leu Val Thr Val
            100                 105                 110

Ser Ser

<210> SEQ ID NO 25
<211> LENGTH: 114
<212> TYPE: PRT
<213> ORGANISM: Artificial Sequence
<220> FEATURE:
<223> OTHER INFORMATION: Synthetic

<400> SEQUENCE: 25

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Thr Ile Tyr Trp Val Arg Gln Ala Pro Gly Gln Gly Leu Glu Trp Met
        35                  40                  45

Gly Ser Ile Ile Pro Ile Leu Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Ala Ser His Thr Ile Trp Gly Gln Gly Thr Leu Val Thr Val
            100                 105                 110

Ser Ser

```
<210> SEQ ID NO 26
<211> LENGTH: 118
<212> TYPE: PRT
<213> ORGANISM: Artificial Sequence
<220> FEATURE:
<223> OTHER INFORMATION: Synthetic

<400> SEQUENCE: 26
```

Glu Val Gln Leu Val Glu Thr Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Ser Gly Ser Gly Gly Ser Thr Tyr Tyr Ala Asp Ser Val
    50                  55                  60

Lys Gly Arg Phe Thr Thr Ser Arg Asp Asn Ser Glu Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Ser Tyr Tyr Asp Asp Ala Phe Asp Ile Trp Gly Gln Gly Thr
            100                 105                 110

Leu Val Thr Val Ser Ser
        115

```
<210> SEQ ID NO 27
<211> LENGTH: 128
<212> TYPE: PRT
<213> ORGANISM: Artificial Sequence
<220> FEATURE:
<223> OTHER INFORMATION: Synthetic

<400> SEQUENCE: 27
```

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Gln Ala Ala Gly Phe Pro Gln Pro Tyr Ile
            100                 105                 110

Tyr Gly Met Asp Val Trp Gly Lys Gly Thr Met Val Thr Val Ser Ser
        115                 120                 125

```
<210> SEQ ID NO 28
<211> LENGTH: 110
<212> TYPE: PRT
<213> ORGANISM: Artificial Sequence
<220> FEATURE:
<223> OTHER INFORMATION: Synthetic
```

```
<400> SEQUENCE: 28

Gln Ala Val Val Thr Gln Glu Pro Ser Leu Thr Val Ser Pro Gly Gly
1               5                   10                  15

Thr Val Thr Leu Thr Cys Ala Ser Ser Thr Gly Ala Val Thr Ser Gly
            20                  25                  30

Tyr Ser Pro Asn Trp Phe Gln Arg Pro Gly Gln Ala Pro Arg Ala
        35                  40                  45

Leu Ile Tyr Thr Thr Ser Asn Arg His Ser Trp Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Asp Tyr Tyr Cys Leu Leu Tyr Tyr Gly Gly
                85                  90                  95

Ala Trp Val Phe Gly Gly Gly Thr Lys Leu Thr Val Leu Gly
                100                 105                 110

<210> SEQ ID NO 29
<211> LENGTH: 110
<212> TYPE: PRT
<213> ORGANISM: Artificial Sequence
<220> FEATURE:
<223> OTHER INFORMATION: Synthetic
<220> FEATURE:
<221> NAME/KEY: SITE
<222> LOCATION: (33)..(33)
<223> OTHER INFORMATION: Xaa is N or Y
<220> FEATURE:
<221> NAME/KEY: SITE
<222> LOCATION: (54)..(54)
<223> OTHER INFORMATION: Xaa is S or N

<400> SEQUENCE: 29

Gln Ala Val Val Thr Gln Glu Pro Ser Leu Thr Val Ser Pro Gly Gly
1               5                   10                  15

Thr Val Thr Leu Thr Cys Ala Ser Ser Thr Gly Ala Val Thr Ser Gly
            20                  25                  30

Xaa Thr Pro Asn Trp Phe Gln Gln Arg Pro Gly Gln Ala Pro Arg Ala
        35                  40                  45

Leu Ile Tyr Thr Thr Xaa Asn Arg His Ser Trp Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Asp Tyr Tyr Cys Leu Leu Tyr Tyr Gly Gly
                85                  90                  95

Ala Trp Val Phe Gly Gly Gly Thr Lys Leu Thr Val Leu Gly
                100                 105                 110

<210> SEQ ID NO 30
<211> LENGTH: 108
<212> TYPE: PRT
<213> ORGANISM: Artificial Sequence
<220> FEATURE:
<223> OTHER INFORMATION: Synthetic

<400> SEQUENCE: 30

Glu Thr Thr Leu Thr Gln Ser Pro Ala Thr Leu Ser Leu Ser Pro Gly
1               5                   10                  15

Asp Thr Ala Thr Leu Ser Cys Arg Ala Ser Gln Ser Val Thr Lys Asp
            20                  25                  30

Leu Val Ala Trp Tyr Gln Gln Arg Pro Gly Gln Ala Pro Arg Leu Leu
```

```
                35                  40                  45
Leu Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Arg Ser Pro
                85                  90                  95

Leu Thr Phe Gly Gly Gly Thr Lys Val Glu Ile Lys
            100                 105
```

<210> SEQ ID NO 31
<211> LENGTH: 111
<212> TYPE: PRT
<213> ORGANISM: Artificial Sequence
<220> FEATURE:
<223> OTHER INFORMATION: Synthetic

<400> SEQUENCE: 31

```
Leu Pro Val Leu Thr Gln Pro Pro Ser Val Ser Lys Gly Leu Arg Gln
 1               5                  10                  15

Thr Ala Thr Leu Thr Cys Thr Gly Asn Ser Asn Asn Val Gly Asn Gln
                20                  25                  30

Gly Ala Ala Trp Leu Gln Gln His Gln Gly His Pro Pro Lys Leu Leu
            35                  40                  45

Thr Tyr Arg Thr Asn Asn Arg Pro Ser Gly Ile Ser Glu Arg Phe Ser
 50                  55                  60

Ala Ser Arg Ser Gly Asn Thr Ala Ser Leu Thr Ile Thr Gly Leu Gln
65                  70                  75                  80

Pro Glu Asp Glu Ala Asp Tyr Tyr Cys Ser Gly Trp Asp Ser Ser Leu
                85                  90                  95

Asn Glu Gly Val Phe Gly Gly Gly Thr Lys Leu Thr Val Leu Gly
            100                 105                 110
```

<210> SEQ ID NO 32
<211> LENGTH: 327
<212> TYPE: PRT
<213> ORGANISM: Artificial Sequence
<220> FEATURE:
<223> OTHER INFORMATION: Synthetic

<400> SEQUENCE: 32

```
Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
            115                 120                 125
```

-continued

```
Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 33
<211> LENGTH: 330
<212> TYPE: PRT
<213> ORGANISM: Artificial Sequence
<220> FEATURE:
<223> OTHER INFORMATION: Synthetic

<400> SEQUENCE: 33

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Ala Val Ser His Glu Asp Pro Glu Val Lys Phe Asn Trp
145                 150                 155                 160
```

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
    195                 200                 205

Lys Ala Leu Ala Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 34
<211> LENGTH: 105
<212> TYPE: PRT
<213> ORGANISM: Artificial Sequence
<220> FEATURE:
<223> OTHER INFORMATION: Synthetic

<400> SEQUENCE: 34

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
            85                  90                  95

Lys Thr Val Ala Pro Thr Glu Cys Ser
        100                 105

<210> SEQ ID NO 35
<211> LENGTH: 104
<212> TYPE: PRT
<213> ORGANISM: Artificial Sequence
<220> FEATURE:
<223> OTHER INFORMATION: Synthetic

<400> SEQUENCE: 35

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
 50                  55                  60

Tyr Ala Ala Ser Ser Tyr Leu Ser Leu Thr Pro Glu Gln Trp Lys Ser
 65                  70                  75                  80

His Arg Ser Tyr Ser Cys Gln Val Thr His Glu Gly Ser Thr Val Glu
                 85                  90                  95

Lys Thr Val Ala Pro Thr Glu Cys
            100

<210> SEQ ID NO 36
<211> LENGTH: 107
<212> TYPE: PRT
<213> ORGANISM: Artificial Sequence
<220> FEATURE:
<223> OTHER INFORMATION: Synthetic

<400> SEQUENCE: 36

Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105

<210> SEQ ID NO 37
<211> LENGTH: 342
<212> TYPE: DNA
<213> ORGANISM: Artificial Sequence
<220> FEATURE:
<223> OTHER INFORMATION: Synthetic

<400> SEQUENCE: 37
caggtgcagc tggtgcagtc tggcgccgag gtgaagaagc aggctccag cgtgaaggtg        60 tcctgcaagg cctccggcgg caccttctct cctacacaa tctcctgggt gaggcaggct       120
ccaggacagg gactggagtg gatgggccgg atcatcccta tcctgggcac cgccaactac       180
gctcagaagt tcagggcag agtgaccatc acagccgacg agtctacctc cacagcttat       240
atggagctga gctctctgcg ctccgaggat accgccgtgt actattgtgc ctccgcctcc       300
cacacaatct ggggcaaggg caccctggtg acagtgtcca gc                          342

<210> SEQ ID NO 38
<211> LENGTH: 342
<212> TYPE: DNA
<213> ORGANISM: Artificial Sequence
<220> FEATURE:
<223> OTHER INFORMATION: Synthetic

<400> SEQUENCE: 38

```
caggtgcagc tggtgcagtc cggcgctgag gtgaagaagc ccggcagctc cgtgaaggtg    60
tcctgcaagg cctccggcgg caccttctcc tcctacacca tctactgggt gaggcaagcc   120
cctggccagg gactggagtg gatgggctcc atcatccta tcctgggcac cgccaactac   180
gcccagaagt tccagggaag ggtgaccatc accgccgacg agagcacctc caccgcctac   240
atggagctgt cctccctgcg gtccgaggac accgctgtgt actactgcgc cagcgcttcc   300
cacaccatct ggggccaggg caccctggtg accgtgtcca gc                      342
```

<210> SEQ ID NO 39
<211> LENGTH: 354
<212> TYPE: DNA
<213> ORGANISM: Artificial Sequence
<220> FEATURE:
<223> OTHER INFORMATION: Synthetic

<400> SEQUENCE: 39

```
gaggtgcagc tggtggagac cggaggagga ctggtgcagc caggaggatc cctgagactg    60
agctgcgccg cttctggctt cacatttttcc agctacgcta tgagctgggt cgcccaggct   120
cctggcaagg gactggagtg ggtgtctggc atcagcggct ctggcggctc tacctactat   180
gccgactccg tgaagggcag gttcaccaca tcccgggata cagcgagaa taccctgtat   240 ctgcagatga actccctgag ggccgaggac acagccgtgt actattgtgc cggctcctac   300
tatgacgatg cttttgatat ctggggccag ggcaccctgg tgacagtgtc ttcc          354
```

<210> SEQ ID NO 40
<211> LENGTH: 384
<212> TYPE: DNA
<213> ORGANISM: Artificial Sequence
<220> FEATURE:
<223> OTHER INFORMATION: Synthetic

<400> SEQUENCE: 40

```
caggtgcagc tgcagcagag cggccctgga ctggtgaagc cttcccagac cctgtccctg    60
acctgcgcca tctccggcga ttccgtgtcc tccaacagcg ccgctggaa ctggatcagg    120 cagagcccta gcaggggcct ggagtggctg gaaggaccct actaccggtc caagtggtac   180
aacgactacg ccgtgtccgt gaagtccagg atcaccatca ccccgacac ctccaagaac    240 cagttctccc tgcagctgaa ctccgtgacc cccgaggaca ccgccgtgta ctactgtgcc   300
cgggatcagg ctgccggctt tcctcagcct acatctacg gcatggacgt gtggggcaag   360
ggcaccatgg tgaccgtgtc ctcc                                           384
```

<210> SEQ ID NO 41
<211> LENGTH: 330
<212> TYPE: DNA
<213> ORGANISM: Artificial Sequence
<220> FEATURE:
<223> OTHER INFORMATION: Synthetic

<400> SEQUENCE: 41

```
caggccgtgg tgacccagga gccttccctg accgtgtccc ctggaggcac cgtgaccctg    60
acctgtgctt cctccacagg cgctgtgacc tccggctact ccccccaactg gttccagcag   120 aggcctggcc aggctcctag ggctctgatc tacaccacct ccaacaggca ctcctggacc   180
cctgccaggt tctccggaag cctgctgggc ggaaaggctg ctctgacact gtccggcgtg   240
cagcctgaag acgaggccga ctactactgc ctgctgtact acggcggcgc ctgggtgttc   300
ggcggcggca ccaagctgac agtgctggga                                     330
```

<210> SEQ ID NO 42
<211> LENGTH: 330
<212> TYPE: DNA
<213> ORGANISM: Artificial Sequence
<220> FEATURE:
<223> OTHER INFORMATION: Synthetic

<400> SEQUENCE: 42

```
caggccgtgg tgacccagga gccaagcctg acagtgtctc caggaggaac cgtgacactg      60
acctgcgcct ccagcacagg cgctgtgacc tctggcaaca cacccaattg gttccagcag     120
aggccaggac aggctcctcg ggctctgatc tacaccacat ccaacagaca cagctggacc     180
cctgctcgct tttctggatc cctgctggga ggcaaggccg ctctgacact gtccggagtg     240
cagccagagg acgaggctga ttactattgt ctgctgtact atggaggagc ttgggtgttc     300
ggaggaggaa caaagctgac cgtgctgggc                                       330
```

<210> SEQ ID NO 43
<211> LENGTH: 330
<212> TYPE: DNA
<213> ORGANISM: Artificial Sequence
<220> FEATURE:
<223> OTHER INFORMATION: Synthetic

<400> SEQUENCE: 43

```
caggccgtgg tgacccagga gccaagcctg acagtgtctc caggaggaac cgtgacactg      60
acctgcgcct ccagcacagg cgctgtgacc tctggctaca cacccaactg gttccagcag     120
aggccaggac aggctcctcg ggctctgatc tataccacat ccaatagaca cagctggacc     180
cctgctcgct tttctggatc cctgctggga ggcaaggccg ctctgacact gtccggagtg     240
cagccagagg acgaggctga ttactattgt ctgctgtact atggaggagc ttgggtgttc     300
ggaggaggaa caaagctgac cgtgctgggc                                       330
```

<210> SEQ ID NO 44
<211> LENGTH: 330
<212> TYPE: DNA
<213> ORGANISM: Artificial Sequence
<220> FEATURE:
<223> OTHER INFORMATION: Synthetic

<400> SEQUENCE: 44

```
caggccgtgg tgacccagga gccaagcctg acagtgtctc caggaggaac cgtgacactg      60
acctgcgcct ccagcacagg cgctgtgacc tctggctaca cacccaactg gttccagcag     120
aggccaggac aggctcctcg ggctctgatc tataccacaa acaatagaca ctcctggacc     180
cctgctcgct tttctggatc cctgctggga ggcaaggccg ctctgacact gagcggagtg     240
cagccagagg acgaggctga ttactattgt ctgctgtact atggaggagc ttgggtgttc     300
ggaggaggaa caaagctgac cgtgctgggc                                       330
```

<210> SEQ ID NO 45
<211> LENGTH: 324
<212> TYPE: DNA
<213> ORGANISM: Artificial Sequence
<220> FEATURE:
<223> OTHER INFORMATION: Synthetic

<400> SEQUENCE: 45

```
gagaccaccc tgacccagtc ccccgctaca ctgtccctgt cccctggcga caccgccaca      60
```

| | |
|---|---|
| ctgtcctgca gggcctccca gagcgtgacc aaggacctgg tggcctggta ccagcagagg | 120 |
| cctggacagg cccctaggct gctgctgtac ggcgcttcct ccagggccac aggcatccct | 180 |
| gataggttct ccggcagcgg ctccggcacc gatttcaccc tgaccatctc caggctggag | 240 |
| cccgaggact cgccgtgta ctactgccag cagtacggca ggtccccct gacctttgga | 300 |
| ggcggcacca aggtggagat caag | 324 |

<210> SEQ ID NO 46
<211> LENGTH: 333
<212> TYPE: DNA
<213> ORGANISM: Artificial Sequence
<220> FEATURE:
<223> OTHER INFORMATION: Synthetic

<400> SEQUENCE: 46

| | |
|---|---|
| ctgcccgtgc tgacccagcc tccttccgtg agcaagggcc tgaggcagac agccaccctg | 60 |
| acctgcaccg gcaactccaa caacgtgggc aaccagggcg ctgcttggct gcagcagcac | 120 |
| cagggccacc ctcctaagct gctgacctac aggaccaaca caggccctc cggcatctcc | 180 |
| gagaggttct ccgcctctag gtccggcaac accgcctccc tgaccatcac cggactgcag | 240 |
| cccgaggacg aggccgacta ctactgctcc ggctgggaca gctccctgaa cgagggcgtg | 300 |
| ttcggcggcg gcaccaagct gacagtgctg gga | 333 |

<210> SEQ ID NO 47
<211> LENGTH: 981
<212> TYPE: DNA
<213> ORGANISM: Artificial Sequence
<220> FEATURE:
<223> OTHER INFORMATION: Synthetic

<400> SEQUENCE: 47

| | |
|---|---|
| gctagcacaa agggaccttc cgtgttccca ctggcccct gctccagaag cacatctgag | 60 |
| tccaccgccg ctctgggctg tctggtgaag gactacttcc ctgagccagt gaccgtgtcc | 120 |
| tggaacagcg gcgccctgac atccggagtg cacacctttc ccgccgtgct ccagtccagc | 180 |
| ggactgtaca gcctgtcttc cgtggtgaca gtgcccagct cttccctggg caccaagaca | 240 |
| tatacctgca acgtggacca taagcctagc aataccaagg tggataagag ggtggagtct | 300 |
| aagtacggac caccttgccc accatgtcca gctcctgagt ttctggggagg accatccgtg | 360 |
| ttcctgtttc ctccaaagcc taaggacacc ctgatgatct ctcggacacc tgaggtgacc | 420 |
| tgcgtggtgg tggacgtgtc ccaggaggac cccgaggtgc agttcaactg gtacgtggat | 480 |
| ggcgtggagg tgcacaatgc taagaccaag ccaagagagg agcagtttaa tagcacatac | 540 |
| cgcgtggtgt ctgtgctgac cgtgctgcat caggattggc tgaacggcaa ggagtataag | 600 |
| tgcaaggtga gcaataaggg cctgcccagc tctatcgaga agacaatctc taaggctaag | 660 |
| ggacagcctc gcgagccaca ggtgtacacc ctgccccctt cccaggagga gatgacaaag | 720 |
| aaccaggtga gcctgacctg tctggtgaag ggcttctatc catctgacat cgctgtggag | 780 |
| tgggagtcca acggccagcc cgagaacaat tacaagacca ccaccccgt gctggactct | 840 |
| gatggctcct tctttctgta ttccaggctg acagtggata gagccggtg gcaggagggc | 900 |
| aacgtgttta gctgctctgt gatgcacgag gctctgcaca atcattatac ccagaagtcc | 960 |
| ctgagcctgt ctctgggcaa g | 981 |

<210> SEQ ID NO 48
<211> LENGTH: 993

<212> TYPE: DNA
<213> ORGANISM: Artificial Sequence
<220> FEATURE:
<223> OTHER INFORMATION: Synthetic

<400> SEQUENCE: 48

```
gctagcacca agggaccatc cgtgttccca ctggccccct ccagcaagtc caccagcgga    60
ggaacagccg ctctgggatg cctggtgaag gactacttcc cagagcccgt gacagtgagc   120
tggaactctg gcgccctgac cagcggagtg cacacatttc cgccgtgct ccagtcttcc    180
ggcctgtact ctctgagctc tgtggtgacc gtgccctcca gctctctggg cacccagaca   240
tatatctgca acgtgaatca caagccaagc aatacaaagg tggacaagaa ggtggagccc   300
aagtcttgtg ataagaccca tacatgcccc ccttgtcctg ctccagaggc tgctggagga   360
ccaagcgtgt tcctgtttcc acccaagcct aaggacaccc tgatgatctc caggaccccc   420
gaggtgacat gcgtggtggt ggctgtgagc cacgaggacc ccgaggtgaa gtttaactgg   480
tacgtggatg gcgtggaggt gcataatgct aagaccaagc taggagga gcagtacaac    540
tctacctatc gggtggtgtc cgtgctgaca gtgctgcacc aggactggct gaacggcaag   600
gagtataagt gcaaggtgtc taataaggcc ctggctgctc ctatcgagaa gaccatctcc   660
aaggccaagg gccagcctag agagccacag gtgtacacac tgcctccatc tcgcgacgag   720
ctgaccaaga accaggtgtc cctgacatgt ctggtgaagg gcttctatcc ttccgacatc   780
gctgtggagt gggagagcaa cggccagcca gagaacaatt acaagaccac ccccctgtg    840
ctggactccg atggcagctt ctttctgtat agcaagctga ccgtggataa gtccaggtgg   900
cagcagggca acgtgttttc ttgctccgtg atgcatgagg ctctgcacaa tcattataca   960
cagaagagcc tgtctctgtc ccctggcaag tga                                993
```

<210> SEQ ID NO 49
<211> LENGTH: 318
<212> TYPE: DNA
<213> ORGANISM: Artificial Sequence
<220> FEATURE:
<223> OTHER INFORMATION: Synthetic

<400> SEQUENCE: 49

```
cagcccaagg ctgccccttc cgtgaccctg tttcccccct cctccgagga gctgcaggcc    60
aacaaggcca ccctggtgtg cctgatctcc gacttctacc ctggcgctgt gaccgtggct   120
tggaaggccg attcctcccc tgtgaaggcc ggcgtggaga ccacaacccc ctccaagcag   180
tccaacaaca agtacgccgc ttcctcctac ctgtccctga cccccgagca gtggaagtcc   240
cacaggtcct actcctgcca ggtgacccac gagggctcca ccgtggagaa gacagtggcc   300
cccaccgagt gctcctga                                                 318
```

<210> SEQ ID NO 50
<211> LENGTH: 324
<212> TYPE: DNA
<213> ORGANISM: Artificial Sequence
<220> FEATURE:
<223> OTHER INFORMATION: Synthetic

<400> SEQUENCE: 50

```
cgtacggtgg ccgctccatc cgtgttcatc tttccccta gcgacgagca gctgaagagc    60
ggcaccgcct ctgtggtgtg cctgctgaac aatttctacc ccaggaggc caaggtgcag   120
tggaaggtgg ataacgctct ccagagcggc aattctcagg agtccgtgac cgagcaggac   180
```

```
agcaaggatt ctacatattc cctgtccagc accctgacac tgtctaaggc cgactacgag    240
aagcacaagg tgtatgcttg cgaggtgaca catcagggcc tgtcttcccc cgtgacaaag    300
tcctttaacc ggggcgagtg ttga                                           324
```

<210> SEQ ID NO 51
<211> LENGTH: 15
<212> TYPE: PRT
<213> ORGANISM: Artificial Sequence
<220> FEATURE:
<223> OTHER INFORMATION: Synthetic

<400> SEQUENCE: 51

```
Gly Gly Gly Gly Ser Gly Gly Gly Gly Ser Gly Gly Gly Gly Ser
1               5                   10                  15
```

<210> SEQ ID NO 52
<211> LENGTH: 654
<212> TYPE: PRT
<213> ORGANISM: Artificial Sequence
<220> FEATURE:
<223> OTHER INFORMATION: Homo Sapiens

<400> SEQUENCE: 52

```
Gln Val Gln Leu Gln Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Ser Gly Ser Thr Tyr Tyr Ala Asp Ser Val
    50                  55                  60

Lys Gly Arg Ser Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Gly Gly Tyr Trp Gly Gln Gly Thr Leu Val Thr Val Ser Ser
            100                 105                 110

Ala Ser Thr Lys Gly Pro Ser Val Phe Pro Leu Ala Pro Cys Ser Arg
        115                 120                 125

Ser Thr Ser Glu Ser Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Lys Thr
            180                 185                 190

Tyr Thr Cys Asn Val Asp His Lys Pro Ser Asn Thr Lys Val Asp Lys
        195                 200                 205

Arg Val Glu Ser Lys Tyr Gly Pro Pro Cys Pro Pro Cys Pro Ala Pro
    210                 215                 220

Glu Phe Leu Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser Gln Glu Asp Pro Glu Val Gln Phe Asn Trp Tyr Val Asp
            260                 265                 270
```

Gly Val Glu Val His Asn Ala Lys Thr Lys Pro Arg Glu Glu Gln Phe
            275                 280                 285

Asn Ser Thr Tyr Arg Val Val Ser Val Leu Thr Val Leu His Gln Asp
    290                 295                 300

Trp Leu Asn Gly Lys Glu Tyr Lys Cys Lys Val Ser Asn Lys Gly Leu
305                 310                 315                 320

Pro Ser Ser Ile Glu Lys Thr Ile Ser Lys Ala Lys Gly Gln Pro Arg
                325                 330                 335

Glu Pro Gln Val Tyr Thr Leu Pro Pro Ser Gln Glu Glu Met Thr Lys
            340                 345                 350

Asn Gln Val Ser Leu Thr Cys Leu Val Lys Gly Phe Tyr Pro Ser Asp
        355                 360                 365

Ile Ala Val Glu Trp Glu Ser Asn Gly Gln Pro Glu Asn Asn Tyr Lys
    370                 375                 380

Thr Thr Pro Pro Val Leu Asp Ser Asp Gly Ser Phe Phe Leu Tyr Ser
385                 390                 395                 400

Arg Leu Thr Val Asp Lys Ser Arg Trp Gln Glu Gly Asn Val Phe Ser
                405                 410                 415

Cys Ser Val Met His Glu Ala Leu His Asn His Tyr Thr Gln Lys Ser
            420                 425                 430

Leu Ser Leu Ser Leu Gly Lys Asp Ile Arg Leu Thr Gln Ser Pro Ser
        435                 440                 445

Ser Leu Ser Ala Ser Val Gly Asp Arg Val Thr Ile Thr Cys Arg Ala
    450                 455                 460

Ser Gln Ser Ile Ser Ser Tyr Leu Asn Trp Tyr Gln Gln Lys Pro Gly
465                 470                 475                 480

Lys Ala Pro Lys Leu Leu Ile Tyr Ala Ala Ser Ser Leu Gln Gly Gly
                485                 490                 495

Val Pro Ser Arg Phe Ser Gly Ser Gly Ser Gly Thr Asp Phe Thr Leu
            500                 505                 510

Thr Ile Ser Ser Leu Gln Pro Glu Asp Ser Ala Thr Tyr Tyr Cys Gln
        515                 520                 525

Gln Ser Tyr Ser Thr Pro Tyr Thr Phe Gly Gln Gly Thr Lys Leu Thr
    530                 535                 540

Val Leu Gly Arg Thr Val Ala Ala Pro Ser Val Phe Ile Phe Pro Pro
545                 550                 555                 560

Ser Asp Glu Gln Leu Lys Ser Gly Thr Ala Ser Val Val Cys Leu Leu
                565                 570                 575

Asn Asn Phe Tyr Pro Arg Glu Ala Lys Val Gln Trp Lys Val Asp Asn
            580                 585                 590

Ala Leu Gln Ser Gly Asn Ser Gln Glu Ser Val Thr Glu Gln Asp Ser
        595                 600                 605

Lys Asp Ser Thr Tyr Ser Leu Ser Ser Thr Leu Thr Leu Ser Lys Ala
    610                 615                 620

Asp Tyr Glu Lys His Lys Val Tyr Ala Cys Glu Val Thr His Gln Gly
625                 630                 635                 640

Leu Ser Ser Pro Val Thr Lys Ser Phe Asn Arg Gly Glu Cys
                645                 650

<210> SEQ ID NO 53
<211> LENGTH: 444
<212> TYPE: PRT
<213> ORGANISM: Artificial Sequence
<220> FEATURE:

<223> OTHER INFORMATION: Synthetic

<400> SEQUENCE: 53

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asn Met His Trp Val Arg Gln Ala Pro Gly Gln Gly Leu Glu Trp Ile
        35                  40                  45

Gly Asp Ile Tyr Pro Gly Ser Gly Asp Thr Ser Tyr Asn Gln Lys Phe
    50                  55                  60

Lys Gly Arg Ala Thr Met Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Gly Gly Ala Phe Pro Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400
```

```
Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly
        435                 440

<210> SEQ ID NO 54
<211> LENGTH: 218
<212> TYPE: PRT
<213> ORGANISM: Artificial Sequence
<220> FEATURE:
<223> OTHER INFORMATION: Synthetic

<400> SEQUENCE: 54

Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Glu Tyr Tyr
            20                  25                  30

Gly Thr Ser Leu Met Gln Trp Tyr Gln Gln Lys Pro Gly Gln Pro Pro
        35                  40                  45

Lys Leu Leu Ile Tyr Ala Ala Ser Asn Val Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Arg
                85                  90                  95

Lys Asp Pro Ser Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 55
<211> LENGTH: 387
<212> TYPE: PRT
<213> ORGANISM: Artificial Sequence
<220> FEATURE:
<223> OTHER INFORMATION: Synthetic

<400> SEQUENCE: 55

Ser Glu Val Glu Tyr Arg Ala Glu Val Gly Gln Asn Ala Tyr Leu Pro
1               5                   10                  15

Cys Phe Tyr Thr Pro Ala Ala Pro Gly Asn Leu Val Pro Val Cys Trp
            20                  25                  30

Gly Lys Gly Ala Cys Pro Val Phe Glu Cys Gly Asn Val Val Leu Arg
        35                  40                  45
```

Thr Asp Glu Arg Asp Val Asn Tyr Trp Thr Ser Arg Tyr Trp Leu Asn
        50                  55                  60

Gly Asp Phe Arg Lys Gly Asp Val Ser Leu Thr Ile Glu Asn Val Thr
 65                  70                  75                  80

Leu Ala Asp Ser Gly Ile Tyr Cys Cys Arg Ile Gln Ile Pro Gly Ile
                 85                  90                  95

Met Asn Asp Glu Lys Phe Asn Leu Lys Leu Val Ile Lys Pro Ala Lys
            100                 105                 110

Val Thr Pro Ala Pro Thr Arg Gln Arg Asp Phe Thr Ala Ala Phe Pro
        115                 120                 125

Arg Met Leu Thr Thr Arg Gly His Gly Pro Ala Glu Thr Gln Thr Leu
    130                 135                 140

Gly Ser Leu Pro Asp Ile Asn Leu Thr Gln Ile Ser Thr Leu Ala Asn
145                 150                 155                 160

Val Pro Arg Asp Cys Gly Cys Lys Pro Cys Ile Cys Thr Val Pro Glu
                165                 170                 175

Val Ser Ser Val Phe Ile Phe Pro Pro Lys Pro Lys Asp Val Leu Thr
            180                 185                 190

Ile Thr Leu Thr Pro Lys Val Thr Cys Val Val Val Asp Ile Ser Lys
        195                 200                 205

Asp Asp Pro Glu Val Gln Phe Ser Trp Phe Val Asp Asp Val Glu Val
    210                 215                 220

His Thr Ala Gln Thr Gln Pro Arg Glu Glu Gln Phe Asn Ser Thr Phe
225                 230                 235                 240

Arg Ser Val Ser Glu Leu Pro Ile Met His Gln Asp Trp Leu Asn Gly
                245                 250                 255

Lys Glu Phe Lys Cys Arg Val Asn Ser Ala Ala Phe Pro Ala Pro Ile
            260                 265                 270

Glu Lys Thr Ile Ser Lys Thr Lys Gly Arg Pro Lys Ala Pro Gln Val
        275                 280                 285

Tyr Thr Ile Pro Pro Pro Lys Glu Gln Met Ala Lys Asp Lys Val Ser
    290                 295                 300

Leu Thr Cys Met Ile Thr Asp Phe Phe Pro Glu Asp Ile Thr Val Glu
305                 310                 315                 320

Trp Gln Trp Asn Gly Gln Pro Ala Glu Asn Tyr Lys Asn Thr Gln Pro
                325                 330                 335

Ile Met Asp Thr Asp Gly Ser Tyr Phe Val Tyr Ser Lys Leu Asn Val
            340                 345                 350

Gln Lys Ser Asn Trp Glu Ala Gly Asn Thr Phe Thr Cys Ser Val Leu
        355                 360                 365

His Glu Gly Leu His Asn His His Thr Glu Lys Ser Leu Ser His Ser
    370                 375                 380

Pro Gly Lys
385

<210> SEQ ID NO 56
<211> LENGTH: 451
<212> TYPE: PRT
<213> ORGANISM: Artificial Sequence
<220> FEATURE:
<223> OTHER INFORMATION: Synthetic

<400> SEQUENCE: 56

Gln Val Gln Leu Gln Gln Pro Gly Ala Glu Leu Val Lys Pro Gly Ala
 1               5                  10                  15

```
Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
            35                  40                  45

Gly Ala Ile Tyr Pro Gly Asn Gly Asp Thr Ser Tyr Asn Gln Lys Phe
50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
            115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430
```

```
<210> SEQ ID NO 57
<211> LENGTH: 213
<212> TYPE: PRT
<213> ORGANISM: Artificial Sequence
<220> FEATURE:
<223> OTHER INFORMATION: Synthetic

<400> SEQUENCE: 57

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

ANTIBODY BINDING TIM-3 AND USE THEREOF

CROSS REFERENCE TO RELATED APPLICATIONS

This application is a national stage filing under 35 U.S.C. § 371 of International Application No. PCT/CN2019/082318, filed Apr. 11, 2019, which claims priority to U.S. Provisional Application No. 62/656,358, filed Apr. 12, 2018, the entire contents of each of which are incorporated herein by reference.

TECHNICAL FIELD

The present invention relates generally to an isolated monoclonal antibody, particularly a human monoclonal antibody that specifically binds to TIM-3 with good therapeutic characteristics. A nucleic acid molecule encoding the antibody, an expression vector, a host cell and a method for expressing the antibody are also provided. The present invention further provides an immunoconjugate, a bispecific molecule and a pharmaceutical composition comprising the antibody, as well as a diagnostic and treatment method using an anti-TIM-3 antibody of the invention.

REFERENCE TO SEQUENCE LISTING SUBMITTED AS A TEXT FILE VIA EFS-WEB

The present application contains a sequence listing which has been submitted in ASCII format via EFS-Web and is hereby incorporated by reference in its entirety. Said ASCII copy, created on Jan. 13, 2021, is named N064070001US00-SEQ-JDH and is 53,269 bytes in size.

BACKGROUND

Therapeutic antibodies are one of the fastest growing segments of the pharmaceutical industry, especially monoclonal antibodies targeting certain disease-related cellular proteins.

One such target protein is T-cell immunoglobulin and mucin-domain containing-3, also known as TIM-3, a protein encoded by the HAVCR2 gene in humans. TIM-3 is an immune checkpoint and expressed as cell surface receptors on IFNγ-producing CD4+ T helper 1(Th1) and CD8$^+$ T cytotoxic1(Tc1) cells, Th17 cells, regulatory T cells and innate immune cells (dendritic cells, NK cells and monocytes) (Monney L et al., (2002) *Nature.* 415 (6871): 536-41; Hastings W I) et al., (2009) *European Journal of Immunology.* 39 (9): 2492-501; Gao X et al., (2012) PLOS One. 7 (2): e30676; Gleason M K et al, (2012) *Blood.* 119 (13): 3064-72). Several ligands were discovered for TIM-3, including galectin-9, PtdSer, HMGB1 and CEACAM1. Among these, galectin-9 and PtdSer are the ones that primarily activates TIM-3, and the ligand engagement limits the duration and magnitude of CD4$^+$ Th1 and CD8+ Tc1 cell responses (Sabatos C A et al., (2003) *Nat Immunol* 4:1102-10; Sabatos-Peyton C A et al., (2018) *ONCOIMMUNOLOGY* 7(2): e1385690)

Preclinical studies using antibodies to block TIM-3 for cancer treatment showed enhanced activation of antigen-specific T cells at the tumor site and disruption of tumor growth. Furthermore, dual anti-TIM-3/anti-PD-1 antibody treatment cured most mice having established tumors that were largely resistant to single antibody treatment (Ngiow S F et al., (2011) *Cancer Res* 71:3540-51).

Despite the promising therapeutic effects, only a few anti-TIM-3 antibodies have been developed till now. One such antibody is MBG-453 of Novartis, the humanized one of ABTIM3 as described in US2015218274A1, which was proved to block TIM-3-PtdSer interaction and is now under phase I trial. Another anti-TIM-3 antibody is described in WO2017/079115 to inhibit binding of TIM-3 to galectin-9.

SUMMARY OF THE INVENTION

The present invention provides an isolated monoclonal antibody, for example, a human, mouse, chimeric or humanized monoclonal antibody, that binds to TIM-3 and has comparable or better pharmaceutical characteristics compared to existing anti-TIM-3 antibodies such as ABTIM3.

In one aspect, the invention pertains to an isolated monoclonal antibody (e.g., a human antibody), or an antigen-binding portion thereof, having a heavy chain variable region that comprises a CDR1 region, a CDR2 region and a CDR3 region, wherein the CDR1 region, the CDR2 region and the CDR3 region comprise amino acid sequences having at least 80%, 85%, 90%, 95%, 98%, 99% or 100% identity to (1) SEQ ID NOs: 1, 5 and 9, respectively; (2) SEQ ID NOs: 2, 6 and 9, respectively; (3) SEQ ID NOs: 3, 7 and 10, respectively; or (4) SEQ ID NOs: 4, 8 and 11, respectively, wherein the antibody or antigen-binding fragment thereof binds TIM-3.

In one aspect, an isolated monoclonal antibody (e.g., a human antibody), or an antigen-binding portion thereof, of the present invention comprises a heavy chain variable region comprising an amino acid sequence having at least 80%, 85%, 90%, 95%, 98%, 99% or 100% identity to SEQ ID NOs: 24, 25, 26 or 27, wherein the antibody or antigen-binding fragment thereof binds TIM-3. These amino acid sequences may be encoded by the nucleotide sequences set forth in SEQ ID NOs: 37, 38, 39 and 40, respectively.

The monoclonal antibody or an antigen-binding portion thereof of the present invention in one embodiment comprises a light chain variable region that comprises a CDR1 region, a CDR2 region and a CDR3 region, wherein the CDR1 region, the CDR2 region and the CDR3 region comprise amino acid sequences having at least 80%, 85%, 90%, 95%, 98%, 99% or 100% identity to (1) SEQ ID NOs: 12, 17 and 21, respectively; (2) SEQ ID NOs: 13, 17 and 21, respectively; (3) SEQ ID NOs: 14, 17 and 21, respectively; (4) SEQ ID NOs: 14, 18 and 21, respectively; (5) SEQ ID NOs: 15, 19 and 22, respectively; or (6) SEQ ID NOs: 16, 20 and 23, respectively; wherein the antibody or antigen-binding fragment thereof binds TIM-3.

In one aspect, an isolated monoclonal antibody (e.g., a human antibody), or an antigen-binding portion thereof, of the present invention comprises a light chain variable region comprising an amino acid sequence having at least 80%, 85%, 90%, 95%, 98%, 99% or 100% identity to SEQ ID NOs: 28, 29 ($X_1$=N, $X_2$=S, or $X_1$=Y, $X_2$=S; $X_1$=Y, $X_2$=N), 30, or 31, wherein the antibody or antigen-binding fragment thereof binds TIM-3. These amino acid sequences may be encoded by the nucleotide sequences set forth in SEQ ID NOs: 41, 42, 43, 44, 45 and 46, respectively.

In one aspect, an isolated monoclonal antibody, or an antigen-binding portion thereof, of the present invention comprises a heavy chain variable region and a light chain variable region each comprising a CDR1 region, a CDR2 region and a CDR3 region, wherein the heavy chain variable region CDR1, CDR2 and CDR3, and the light chain variable region CDR1, CDR2 and CDR3 comprise amino acid sequences having at least 80%, 85%, 90%, 95%, 98%, 99% or 100% identity to (1) SEQ ID NOs: 1, 5, 9, 12, 17 and 21, respectively; (2) SEQ ID NOs: 2, 6, 9, 13, 17 and 21, respectively; (3) SEQ ID NOs: 2, 6, 9, 14, 17 and 21, respectively; (4) SEQ ID NOs: 2, 6, 9, 14, 18 and 21, respectively; (5) SEQ ID NOs: 3, 7, 10, 15, 19 and 22, respectively; or (6) SEQ ID NOs: 4, 8, 11, 16, 20 and 23, respectively, wherein the antibody or antigen-binding fragment thereof binds to TIM-3.

In one embodiment, the antibody, or the antigen-binding portion thereof, comprises a heavy chain variable region and a light chain variable region, the heavy chain variable region and the light chain variable region comprising amino acid sequences having at least 80%, 85%, 90%, 95%, 98%, 99% or 100% identity to (1) SEQ ID NOs: 24 and 28, respectively; (2) SEQ ID NOs: 25 and 29 ($X_1$=N, $X_2$=S, or $X_1$=Y, $X_2$=S; $X_1$=Y, $X_2$=N), respectively; (3) SEQ ID NOs: 26 and 30, respectively; or (4) SEQ ID NOs: 27 and 31, respectively, wherein the antibody or antigen-binding fragment thereof binds TIM-3.

In one embodiment, an isolated monoclonal antibody, or the antigen-binding portion thereof, of the present invention comprises a heavy chain and a light chain, the heavy chain comprising a heavy chain variable region and a heavy chain constant region, the light chain comprising a light chain variable region and a light chain constant region, wherein, the heavy chain constant region comprises amino acid sequences having at least 80%, 85%, 90%, 95%, 98%, 99% or 100% identity to SEQ ID No: 32 or 33, and the light chain constant region comprises amino acid sequences having at least 80%, 85%, 90%, 95%, 98%, 99% or 100% identity to SEQ ID No: 34, 35, or 36, and the heavy chain variable region and the light chain variable region comprise amino acid sequences described above, wherein the antibody or antigen-binding fragment thereof binds to TIM-3. The amino acid sequences of SEQ ID NOs: 32, 33, 34 and 36 may be encoded by the nucleotide sequences set forth in SEQ ID NOs: 47, 48, 49 and 50, respectively. The heavy chain constant region is specially designed such that the anti-TIM-3 antibody does not induce Antibody-Dependent Cell-Mediated Cytotoxicity (ADCC) or Complement-Dependent Cytotoxicity (CDC) on TIM-3-expressing cells. For example, human IgG1 heavy chain may contain L234A, L235A, D265A and/or P329A (EU numbering) mutations for elimination of ADCC or CDC function.

The antibody of the invention can be a full-length antibody, for example, of an IgG1, IgG2 or IgG4 isotype. The antibody of the present invention in other embodiments may be a single chain antibody, or consists of antibody fragments, such as Fab or Fab'2 fragments.

The antibody, or the antigen-binding portion thereof, of the invention, binds to human TIM-3 with a $K_D$ of about $2.05 \times 10^{-9}$ M or less, inhibits the binding of TIM-3 to galectin-9, ptdSer or other ligands, does not cross react with TIM-1 or TIM-4, induces TIM-3 internalization on cell membrane, induces pre-stimulated human T cells to release IL-2 and/or IFNγ, does not induce ADCC or CDC on TIM-3-expressing cells, and/or enhances activation of antigen specific CD4+ or CD8+ T cells. The antibody, or the antigen-binding portion thereof, of the invention, has comparable, if not better, binding and/or blocking activity compared to prior art anti-TIM-3 antibodies such as ABTIM3.

The invention also provides an immunoconjugate comprising an antibody of the invention, or antigen-binding portion thereof, linked to a therapeutic agent, such as a cytotoxin. The invention also provides a bispecific molecule comprising an antibody, or antigen-binding portion thereof, of the invention, linked to a second functional moiety (e.g., a second antibody) having a different binding specificity than said antibody, or antigen-binding portion thereof. In another aspect, the antibody or an antigen-binding portions thereof of the present invention can be made into part of a chimeric antigen receptor (CAR). The antibody or an antigen-binding portions thereof of the present invention can also be encoded by or used in conjunction with an oncolytic virus.

Compositions comprising an antibody, or antigen-binding portion thereof, or immunoconjugate, bispecific molecule, or CAR of the invention, and a pharmaceutically acceptable carrier, are also provided.

Nucleic acid molecules encoding the antibodies, or antigen-binding portions thereof, of the invention are also encompassed by the invention, as well as expression vectors comprising such nucleic acids and host cells comprising such expression vectors. A method for preparing an anti-TIM-3 antibody using the host cell comprising the expression vector is also provided, comprising steps of (i) expressing the antibody in the host cell and (ii) isolating the antibody from the host cell or its cell culture.

In another embodiment, the invention provides a method for enhancing an immune response in a subject comprising administering to the subject an antibody, or an antigen-binding portion thereof, of the invention. In another embodiment, at least one additional immunostimulatory antibody can be administered with the antibody, or an antigen-binding portion there, of the invention, such as an anti-PD-1 antibody, an anti-LAG-3 antibody and/or an anti-CTLA-4 antibody, such that an immune response is enhanced in the subject, for example to inhibit tumor growth or to stimulate an anti-viral response. In one embodiment, the additional immunostimulatory antibody is an anti-PD-1 antibody. In another embodiment, the additional immunostimulatory agent is an anti-LAG-3 antibody. In yet another embodiment, the additional immunostimulatory agent is an anti-CTLA-4 antibody. In yet another embodiment, an antibody, or an antigen-binding portion thereof, of the invention is administered with a cytokine (e.g., IL-2 and/or IL-21), or a costimulatory antibody (e.g., an anti-CD137 and/or anti-GITR antibody). The antibodies can be, for example, mouse, human, chimeric or humanized antibodies.

In another embodiment, the invention provides a method for treating a tumor or cancer in a subject, comprising administering to the subject an antibody, or an antigen-binding portion thereof, of the invention. The cancer may be a solid or non-solid tumor, including, but not limited to, B cell lymphoma, chronic lymphocytic leukemia, multiple myeloma, melanoma, colon adenocarcinoma, pancreas cancer, colon cancer, gastric intestine cancer, prostate cancer, bladder cancer, kidney cancer, ovary cancer, cervix cancer, breast cancer, lung cancer, and nasopharynx cancer. In some embodiments, the method comprises administering a composition, a bispecific molecule, an immunoconjugate, a CAR-T cell, or an antibody-encoding or antibody-bearing oncolytic virus of the invention. In some embodiments, at least one additional anti-cancer antibody can be administered with the antibody, or an antigen-binding portion thereof, of the invention, such as an anti-VISTA antibody, an anti-PD-1 antibody, an anti-PD-L1 antibody, an anti-LAG-3 antibody and/or an anti-CTLA-4 antibody. In yet another embodiment, an antibody, or an antigen-binding portion thereof, of the invention is administered with a cytokine (e.g., IL-2 and/or IL-21), or a costimulatory antibody (e.g., an anti-CD137 and/or anti-GITR antibody). In another embodiment, an antibody, or an antigen-binding portion thereof, of the invention is administered with a chemotherapeutic agent, which may be a cytotoxic agent, such as epirubicin, oxaliplatin, and/or 5-fluorouracil (5-FU). The antibodies of the present invention can be, for example, mouse, human, chimeric or humanized antibodies.

In still another embodiment, the invention provides a method for treating viral infection in a subject, comprising administering to the subject an antibody, or an antigen-binding portion thereof, of the invention.

In another aspect, the invention provides an anti-TIM-3 antibody and a composition of the invention for use in the foregoing methods, or for the manufacture of a medicament for use in the foregoing methods (e.g., for treatment).

Other features and advantages of the instant invention will be apparent from the following detailed description and examples which should not be construed as limiting. The contents of all references, GenBank entries, patents and published patent applications cited throughout this application are expressly incorporated herein by reference.

DETAILED DESCRIPTION OF THE INVENTION

Figure 1:
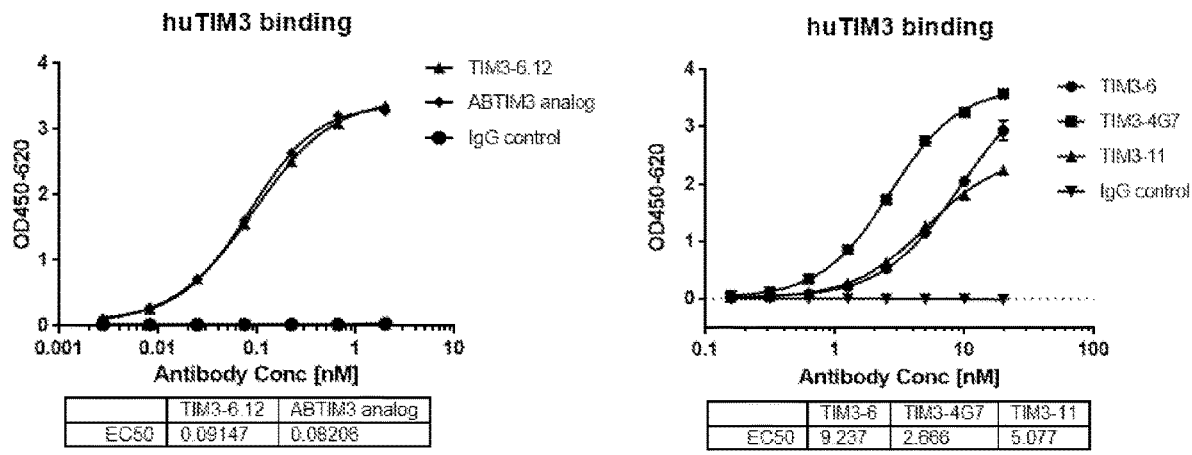
FIG. 1 shows the binding activity of anti-TIM-3 antibodies TIM3-6.12 (left panel), TIM3-6, TIM3-4G7 and TIM3-11 (right panel) to human TIM-3.

In order that the present disclosure may be more readily understood, certain terms are first defined. Additional definitions are set forth throughout the detailed description.

The term "TIM-3" refers to T-cell immunoglobulin and mucin-domain containing-3. The term "TIM-3" comprises variants, isoforms, homologs, orthologs and paralogs. For example, an antibody specific for a human TIM-3 protein may, in certain cases, cross-reacts with a TIM-3 protein from a species other than human. In other embodiments, an antibody specific for a human TIM-3 protein may be completely specific for the human TIM-3 protein and exhibit no cross-reactivity to other species or of other types, or may cross-react with TIM-3 from certain other species but not all other species (e.g., cross-react with monkey TIM-3 but not mouse TIM-3).

The term "human TIM-3" refers to human sequence of TIM-3, such as the complete amino acid sequence of human TIM-3 having Genbank Accession No. NP_116171.

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

The term "antibody" as referred to herein includes whole antibodies and any antigen binding fragment (i.e., "antigen-binding portion") or single chains thereof. Whole antibodies are glycoproteins comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, $C_{H1}$, $C_{H2}$ and $C_{H3}$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system.

The term "antigen-binding portion" of an antibody (or simply "antibody portion"), as used herein, refers to one or more fragments of an antibody that retain the ability to specifically bind to an antigen (e.g., a TIM-3 protein). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; (vi) an isolated complementarity determining region (CDR); and (viii) a nanobody, a heavy chain variable region containing a single variable domain and two constant domains. Furthermore, although the two domains of the Fv fragment, $V_L$ and $V_H$, are coded by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al., (1988) *Science* 242:423-426; and Huston et al., (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

An "isolated antibody", as used herein, is intended to refer to an antibody that is substantially free of other antibodies having different antigenic specificities (e.g., an isolated antibody that specifically binds a TIM-3 protein is substantially free of antibodies that specifically bind antigens other than TIM-3 proteins). An isolated antibody that specifically binds a human TIM-3 protein may, however, have cross-reactivity to other antigens, such as TIM-3 proteins from other species. Moreover, an isolated antibody can be substantially free of other cellular material and/or chemicals.

The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention can include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species have been grafted onto human framework sequences.

The term "mouse antibody", as used herein, is intended to include antibodies having variable regions in which both the framework and CDR regions are derived from mouse germline immunoglobulin sequences. Furthermore, if the antibody contains a constant region, the constant region also is derived from mouse germline immunoglobulin sequences. The mouse antibodies of the invention can include amino acid residues not encoded by mouse germline immunoglobulin sequences (e.g., mutations introduced by random or site-specific mutagenesis in vitro or by somatic mutation in vivo). However, the term "mouse antibody", as used herein, is not intended to include antibodies in which CDR sequences derived from the germline of another mammalian species have been grafted onto mouse framework sequences.

The term "chimeric antibody" refers to an antibody made by combining genetic material from a nonhuman source with genetic material from a human being. Or more generally, a chimeric antibody is an antibody having genetic material from a certain species with genetic material from another species.

The term "humanized antibody", as used herein, refers to an antibody from non-human species whose protein sequences have been modified to increase similarity to antibody variants produced naturally in humans.

The term "human monoclonal antibody" refers to antibodies displaying a single binding specificity, which have variable regions in which both the framework and CDR regions are derived from human germline immunoglobulin sequences.

The term "isotype" refers to the antibody class (e.g., IgM or IgG1) that is encoded by the heavy chain constant region genes.

The phrases "an antibody recognizing an antigen" and "an antibody specific for an antigen" are used interchangeably herein with the term "an antibody which binds specifically to an antigen."

The term "antibody derivatives" refers to any modified form of the antibody, e.g., a conjugate of the antibody and another agent or antibody.

As used herein, an antibody that "specifically binds to human TIM-3" is intended to refer to an antibody that binds to human TIM-3 protein (and possibly a TIM-3 protein from one or more non-human species) but does not substantially bind to non-TIM-3 proteins. Preferably, the antibody binds to a human TIM-3 protein with "high affinity", namely with a $K_D$ of $5\times10^{-9}$ M or less.

The term "does not substantially bind" to a protein or cells, as used herein, means does not bind or does not bind with a high affinity to the protein or cells, i.e. binds to the protein or cells with a $K_D$ of $1\times10^{-6}$ M or more, more preferably $1\times10^{-5}$ M or more, more preferably $1\times10^{-4}$ M or more, more preferably $1\times10^{-3}$ M or more, even more preferably $1\times10^{-2}$ M or more.

The term "$K_{assoc}$" or "$K_a$", as used herein, is intended to refer to the association rate of a particular antibody-antigen interaction, whereas the term "$K_{dis}$" or "$K_d$," as used herein, is intended to refer to the dissociation rate of a particular antibody-antigen interaction. The term "$K_D$", as used herein, is intended to refer to the dissociation constant, which is obtained from the ratio of $K_d$ to $K_a$ (i.e., $K_d/K_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore™ system.

The term "high affinity" for an IgG antibody refers to an antibody having a $K_D$ of $1\times10^{-6}$ M or less, more preferably $5\times10^{-8}$ M or less, even more preferably $1\times10^{-8}$ M or less, even more preferably $5\times10^{-9}$ M or less for a target antigen. However, "high affinity" binding can vary for other antibody isotypes. For example, "high affinity" binding for an IgM isotype refers to an antibody having a $K_D$ of $10^{-6}$ M or less, more preferably $10^{-7}$ M or less, even more preferably $10^{-8}$ M or less.

The term "$IC_{50}$", also known as half maximal inhibitory concentration, refers to the concentration of an antibody which inhibits a specific biological or biochemical function by 50% relative to the absence of the antibody.

The term "$EC_{50}$", also known as half maximal effective concentration, refers to the concentration of an antibody which induces a response halfway between the baseline and maximum after a specified exposure time.

The term "antibody-dependent cellular cytotoxicity", "antibody-dependent cell-mediated cytotoxicity" or "ADCC," as used herein, refers to a mechanism of cell-mediated immune defense whereby an effector cell of the immune system actively lyses a target cell, such as a tumor cell, whose membrane-surface antigens have been bound by antibodies. The antibody of the invention does not induce ADCC on TIM-3-expressing cells so as to protect immune cells.

The term "complement-dependent cytotoxicity" or "CDC" generally refers to an effector function of IgG and IgM antibodies, which trigger classical complement pathway when bound to a surface antigen, inducing formation of a membrane attack complex and target cell lysis. The antibody of the invention does not induce CDC on TIM-3-expressing cells so as to protect immune cells.

The term "subject" includes any human or nonhuman animal. The term "nonhuman animal" includes all vertebrates, e.g., mammals and non-mammals, such as non-human primates, sheep, dogs, cats, cows, horses, chickens, amphibians, and reptiles, although mammals are preferred, such as non-human primates, sheep, dogs, cats, cows and horses.

Various aspects of the invention are described in further detail in the following subsections.

Anti-TIM-3 Antibodies Having Advantageous Functional Properties

Antibodies of the invention specifically bind to human TIM-3. Antibodies of the invention preferably bind to human TIM-3 protein with a $K_D$ of $5\times10^{-9}$ M or less, more preferably with a $K_D$ of $2.5\times10^{-9}$ M or less.

TIM3-6.10, TIM3-6.11 and TIM3-6.12 differ by one or two amino acid residues at the light chain variable region, leading to slightly different affinities to human TIM-3. The three antibodies also have Q at the $106^{th}$ amino acid position, compared to K in TIM3-6. Such an amino acid modification renders these antibodies more stable under stress.

TABLE 1

Amino acid sequences of Anti-TIM-3 Antibodies

| | SEQ ID NO. | | | | | | | | | |
|---|---|---|---|---|---|---|---|---|---|---|
| | Heavy chain | | | | | Light chain | | | | |
| Clone | $V_H$ CDR1 | $V_H$ CDR2 | $V_H$ CDR3 | $V_H$ | $C_H$ | $V_H$ CDR1 | $V_H$ CDR2 | $V_H$ CDR3 | $V_H$ | $C_H$ |
| TIM3-6 | 1 | 5 | 9 | 24 | 32 | 12 | 17 | 21 | 28 | 34 |
| TIM3-6.10 | 2 | 6 | 9 | 25 | 33 | 13 | 17 | 21 | 29 $X_1 = N,$ $X_2 = S$ | 35 |
| TIM3-6.11 | 2 | 6 | 9 | 25 | 33 | 14 | 17 | 21 | 29 $X_1 = Y,$ $X_2 = S$ | 35 |
| TIM3-6.12 | 2 | 6 | 9 | 25 | 33 | 14 | 18 | 21 | 29 $X_1 = Y,$ $X_2 = S$ | 35 |
| TIM3-4G7 | 3 | 7 | 10 | 26 | 32 | 15 | 19 | 22 | 30 | 36 |
| TIM3-11 | 4 | 8 | 11 | 27 | 32 | 16 | 20 | 23 | 31 | 34 |

Antibodies of the invention inhibit the binding of TIM-3 to galectin-9, ptdSer or other ligands. Antibodies of the invention do not cross react with TIM-1 or TIM-4. Antibodies of the invention induce TIM-3 internalization on cell membrane. Antibodies of the invention induce pre-stimulated human T cells to release IL-2 and/or IFNγ, and enhances activation of antigen specific CD4+ or CD8+ T cells. Antibodies of the invention do not induce ADCC or CDC on TIM-3-expressing cells so as to protect immune cells.

The binding activity of the antibody of the invention, is comparable to, if not better than, prior art anti-TIM-3 antibodies such as ABTIM3. The antibodies of the present invention, in one embodiment, can inhibit binding of TIM-3 to galectin-9 in a much lower concentration than ABTIM3.

Preferred antibodies of the invention are fully human monoclonal antibodies.

Monoclonal Anti-TIM-3 Antibody

A preferred antibody of the invention is the monoclonal antibody structurally and chemically characterized as described below and in the following Examples. The $V_H$ amino acid sequence of the anti-TIM-3 antibody is set forth in SEQ ID NOs: 24, 25, 26 or 27. The $V_L$ amino acid sequence of the anti-TIM-3 antibody is shown in SEQ ID NOs: 28, 29, 30, or 31. The amino acid sequence ID numbers of the heavy/light chain variable regions of the antibodies are summarized in Table 1 below, some clones sharing the same $V_H$ or CDR sequences. The heavy chain constant region is specially designed such that the anti-TIM-3 antibody does not induce ADCC or CDC on TIM-3-expressing cells. The heavy chain constant region may have amino acid sequence set forth in SEQ ID NOs: 32 or 33, and the light chain constant region may have amino acid sequence set forth in SEQ ID NOs: 34, 35, or 36.

The CDR regions in Table 1 have been determined by the Kabat numbering system. However, as is well known in the art, CDR regions can also be determined by other systems such as Chothia, CCG, and IMGT system/method, based on heavy chain/light chain variable region sequences.

The $V_H$ and $V_L$ sequences (or CDR sequences) of other anti-TIM-3 antibodies which bind to human TIM-3 can be "mixed and matched" with the $V_H$ and $V_L$ sequences (or CDR sequences) of the anti-TIM-3 antibody of the present invention. Preferably, when $V_H$ and $V_L$ chains (or the CDRs within such chains) are mixed and matched, a $V_H$ sequence from a particular $V_H/V_L$ pairing is replaced with a structurally similar $V_H$ sequence. Likewise, preferably a $V_L$ sequence from a particular $V_H/V_L$ pairing is replaced with a structurally similar $V_L$ sequence.

Accordingly, in one embodiment, an antibody of the invention, or an antigen binding portion thereof, comprises:
(a) a heavy chain variable region comprising an amino acid sequence listed above in Table 1; and
(b) a light chain variable region comprising an amino acid sequence listed above in Table 1, or the $V_L$ of another anti-TIM-3 antibody, wherein the antibody specifically binds human TIM-3.

In another embodiment, an antibody of the invention, or an antigen binding portion thereof, comprises:
(a) the CDR1, CDR2, and CDR3 regions of the heavy chain variable region listed above in Table 1; and
(b) the CDR1, CDR2, and CDR3 regions of the light chain variable region listed above in Table 1 or the CDRs of another anti-TIM-3 antibody, wherein the antibody specifically binds human TIM-3.

In yet another embodiment, the antibody, or antigen binding portion thereof, includes the heavy chain variable CDR2 region of anti-TIM-3 antibody combined with CDRs of other antibodies which bind human TIM-3, e.g., CDR1 and/or CDR3 from the heavy chain variable region, and/or CDR1, CDR2, and/or CDR3 from the light chain variable region of a different anti-TIM-3 antibody.

In addition, it is well known in the art that the CDR3 domain, independently from the CDR1 and/or CDR2 domain(s), alone can determine the binding specificity of an antibody for a cognate antigen and that multiple antibodies can predictably be generated having the same binding specificity based on a common CDR3 sequence. See, e.g., Klimka et al., *British J. of Cancer* 83(2):252-260 (2000); Beiboer et al., *J. Mol. Biol.* 296:833-849 (2000); Rader et al., *Proc. Natl. Acad. Sci. U.S.A.* 95:8910-8915 (1998); Barbas et al., *J. Am. Chem. Soc.* 116:2161-2162 (1994); Barbas et al., *Proc. Natl. Acad. Sci. U.S.A.* 92:2529-2533 (1995); Ditzel et al., *J. Immunol.* 157:739-749 (1996); Berezov et al., *BIA journal* 8: Scientific Review 8 (2001); Igarashi et al., *J. Biochem* (Tokyo) 117:452-7 (1995); Bourgeois et al., *J. Virol* 72:807-10 (1998); Levi et al., *Proc. Natl. Acad. Sci. U.S.A.* 90:4374-8 (1993); *Polymenis and Stoller, J. Immunol.* 152: 5218-5329 (1994) and Xu and Davis, Immunity 13:37-45 (2000). See also, U.S. Pat. Nos. 6,951,646; 6,914,128; 6,090,382; 6,818,216; 6,156,313; 6,827,925; 5,833,943; 5,762,905 and 5,760,185. Each of these references is hereby incorporated by reference in its entirety.

Accordingly, in another embodiment, antibodies of the invention comprise the CDR2 of the heavy chain variable region of the anti-TIM-3 antibody and at least the CDR3 of the heavy and/or light chain variable region of the anti-TIM-3 antibody, or the CDR3 of the heavy and/or light chain variable region of another anti-TIM-3 antibody, wherein the antibody is capable of specifically binding to human TIM-3. These antibodies preferably (a) compete for binding with TIM-3; (b) retain the functional characteristics; (c) bind to the same epitope; and/or (d) have a similar binding affinity as the anti-TIM-3 antibody of the present invention. In yet another embodiment, the antibodies further may comprise the CDR2 of the light chain variable region of the anti-TIM-3 antibody, or the CDR2 of the light chain variable region of another anti-TIM-3 antibody, wherein the antibody is capable of specifically binding to human TIM-3. In another embodiment, the antibodies of the invention may include the CDR1 of the heavy and/or light chain variable region of the anti-TIM-3 antibody, or the CDR1 of the heavy and/or light chain variable region of another anti-TIM-3 antibody, wherein the antibody is capable of specifically binding to human TIM-3.

Conservative Modifications

In another embodiment, an antibody of the invention comprises a heavy and/or light chain variable region sequences of CDR1, CDR2 and CDR3 sequences which differ from those of the anti-TIM-3 antibodies of the present invention by one or more conservative modifications. It is understood in the art that certain conservative sequence modification can be made which do not remove antigen binding. See, e.g., Brummell et al., (1993) *Biochem* 32:1180-8; de Wildt et al., (1997) *Prot. Eng.* 10:835-41; Komissarov et al., (1997) *J. Biol. Chem.* 272:26864-26870; Hall et al., (1992) *J. Immunol.* 149:1605-12; Kelley and O'Connell (1993) *Biochem.* 32:6862-35; Adib-Conquy et al., (1998) *Int. Immunol.* 10:341-6 and Beers et al., (2000) *Clin. Can. Res.* 6:2835-43.

Accordingly, in one embodiment, the antibody comprises a heavy chain variable region comprising CDR1, CDR2, and CDR3 sequences and/or a light chain variable region comprising CDR1, CDR2, and CDR3 sequences, wherein:
  (a) the heavy chain variable region CDR1 sequence comprises a sequence listed in Table 1 above, and/or conservative modifications thereof; and/or
  (b) the heavy chain variable region CDR2 sequence comprises a sequence listed in Table 1 above, and/or conservative modifications thereof; and/or
  (c) the heavy chain variable region CDR3 sequence comprises a sequence listed in Table 1 above, and conservative modifications thereof; and/or (d) the light chain variable region CDR1, and/or CDR2, and/or CDR3 sequences comprise the sequence(s) listed in Table 1 above; and/or conservative modifications thereof; and
  (e) the antibody specifically binds human TIM-3.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for retained function (i.e., the functions set forth above) using the functional assays described herein.

Engineered and Modified Antibodies

Antibodies of the invention can be prepared using an antibody having one or more of the $V_H/V_L$ sequences of the anti-TIM-3 antibody of the present invention as starting material to engineer a modified antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

In certain embodiments, CDR grafting can be used to engineer variable regions of antibodies. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann et al., (1998) *Nature* 332:323-327; Jones et al., (1986) *Nature* 321:522-525; Queen et al., (1989) *Proc. Natl. Acad. See also U.S.A.* 86:10029-10033; U.S. Pat. Nos. 5,225,539; 5,530,101; 5,585,089; 5,693,762 and 6,180,370).

Accordingly, another embodiment of the invention pertains to an isolated monoclonal antibody, or antigen binding portion thereof, comprising a heavy chain variable region comprising CDR1, CDR2, and CDR3 sequences comprising the sequences of the present invention, as described above, and/or a light chain variable region comprising CDR1, CDR2, and CDR3 sequences comprising the sequences of the present invention, as described above. While these antibodies contain the $V_H$ and $V_L$ CDR sequences of the monoclonal antibody of the present invention, they can contain different framework sequences.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat et al., (1991), cited supra; Tomlinson et al., (1992) *J. Mol. Biol.* 227:776-798; and Cox et al., (1994) *Eur. J. Immunol.* 24:827-836; the contents of each of which are expressly incorporated herein by reference. As another example, the germline DNA sequences for human heavy and light chain variable region genes can be found in the Genbank database. For example, the following heavy chain germline sequences found in the HCo7 HuMAb mouse are available in the accompanying Genbank Accession Nos.: 1-69 (NG-0010109, NT-024637 & BC070333), 3-33 (NG-0010109 & NT-024637) and 3-7 (NG-0010109 & NT-024637). As another example, the following heavy chain germline sequences found in the HCo12 HuMAb mouse are available in the accompanying Genbank Accession Nos.: 1-69 (NG-0010109, NT-024637 & BC070333), 5-51 (NG-0010109 & NT-024637), 4-34 (NG-0010109 & NT-024637), 3-30.3 (CAJ556644) & 3-23 (AJ406678).

Antibody protein sequences are compared against a compiled protein sequence database using one of the sequence similarity searching methods called the Gapped BLAST (Altschul et al., (1997), supra), which is well known to those skilled in the art.

Preferred framework sequences for use in the antibodies of the invention are those that are structurally similar to the framework sequences used by antibodies of the invention. The $V_H$ CDR1, CDR2, and CDR3 sequences can be grafted onto framework regions that have the identical sequence as that found in the germline immunoglobulin gene from which the framework sequence derives, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370).

Another type of variable region modification is to mutate amino acid residues within the $V_H$ and/or $V_L$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as known in the art. Preferably conservative modifications (as known in the art) are introduced. The mutations can be amino acid substitutions, additions or deletions, but are preferably substitutions. Moreover, typically no more than one, two, three, four or five residues within a CDR region are altered.

Accordingly, in another embodiment, the invention provides isolated anti-TIM-3 monoclonal antibodies, or antigen binding portions thereof, comprising a heavy chain variable region comprising: (a) a $V_H$ CDR1 region comprising the sequence of the present invention, or an amino acid sequence having one, two, three, four or five amino acid substitutions, deletions or additions; (b) a $V_H$ CDR2 region comprising the sequence of the present invention, or an amino acid sequence having one, two, three, four or five amino acid substitutions, deletions or additions; (c) a $V_H$ CDR3 region comprising the sequence of the present invention, or an amino acid sequence having one, two, three, four or five amino acid substitutions, deletions or additions; (d) a $V_L$ CDR1 region comprising the sequence of the present invention, or an amino acid sequence having one, two, three, four or five amino acid substitutions, deletions or additions; (e) a $V_L$ CDR2 region comprising the sequence of the present invention, or an amino acid sequence having one, two, three, four or five amino acid substitutions, deletions or additions; and (f) a $V_L$ CDR3 region comprising the sequence of the present invention, or an amino acid sequence having one, two, three, four or five amino acid substitutions, deletions or additions.

Engineered antibodies of the invention include those in which modifications have been made to framework residues within $V_H$ and/or $V_L$, e.g. to improve the properties of the antibody. Typically, such framework modifications are made to decrease the immunogenicity of the antibody. For example, one approach is to "backmutate" one or more framework residues to the corresponding germline sequence. More specifically, an antibody that has undergone somatic mutation can contain framework residues that differ from the germline sequence from which the antibody is derived. Such residues can be identified by comparing the antibody framework sequences to the germline sequences from which the antibody is derived.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043.

In addition, or as an alternative to modifications made within the framework or CDR regions, antibodies of the invention can be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention can be chemically modified (e.g., one or more chemical moieties can be attached to the antibody) or be modified to alter its glycosylation, again to alter one or more functional properties of the antibody.

In one embodiment, the hinge region of $C_{H1}$ is modified in such that the number of cysteine residues in the hinge region is altered, e.g., increased or decreased. This approach is described further in U.S. Pat. No. 5,677,425. The number of cysteine residues in the hinge region of $C_{H1}$ is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the $C_{H2}$-$C_{H3}$ domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745.

In still another embodiment, the glycosylation of an antibody is modified. For example, a glycosylated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. See, e.g., U.S. Pat. Nos. 5,714,350 and 6,350,861.

Another modification of the antibodies herein that is contemplated by this disclosure is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono ($C_1$-$C_{10}$) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See, e.g., EPO 154 316 and EP 0 401 384.

Antibody's Physical Properties

Antibodies of the invention can be characterized by their various physical properties, to detect and/or differentiate different classes thereof.

For example, antibodies can contain one or more glycosylation sites in either the light or heavy chain variable region. Such glycosylation sites may result in increased immunogenicity of the antibody or an alteration of the pK of the antibody due to altered antigen binding (Marshall et al (1972) Annu Rev Biochem 41:673-702; Gala and Morrison (2004) J Immunol 172:5489-94; Wallick et al (1988) J Exp Med 168:1099-109; Spiro (2002) Glycobiology 12:43R-56R; Parekh et al (1985) Nature 316:452-7; Mimura et al., (2000) Mol Immunol 37:697-706). Glycosylation has been known to occur at motifs containing an N-X-S/T sequence. In some instances, it is preferred to have an anti-TIM-3 antibody that does not contain variable region glycosylation. This can be achieved either by selecting antibodies that do not contain the glycosylation motif in the variable region or by mutating residues within the glycosylation region.

In a preferred embodiment, the antibodies do not contain asparagine isomerism sites. The deamidation of asparagine may occur on N-G or D-G sequences and result in the creation of an isoaspartic acid residue that introduces a kink into the polypeptide chain and decreases its stability (isoaspartic acid effect).

Each antibody will have a unique isoelectric point (pI), which generally falls in the pH range between 6 and 9.5. The pI for an IgG1 antibody typically falls within the pH range of 7-9.5 and the pI for an IgG4 antibody typically falls within the pH range of 6-8. There is speculation that antibodies with a pI outside the normal range may have some unfolding and instability under in vivo conditions. Thus, it is preferred to have an anti-TIM-3 antibody that contains a pI value that falls in the normal range. This can be achieved either by selecting antibodies with a pI in the normal range or by mutating charged surface residues.

Nucleic Acid Molecules Encoding Antibodies of the Invention

In another aspect, the invention provides nucleic acid molecules that encode heavy and/or light chain variable regions, or CDRs, of the antibodies of the invention. The nucleic acids can be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques. A nucleic acid of the invention can be, e.g., DNA or RNA and may or may not contain intronic sequences. In a preferred embodiment, the nucleic acid is a cDNA molecule.

Nucleic acids of the invention can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), a nucleic acid encoding such antibodies can be recovered from the gene library.

Preferred nucleic acids molecules of the invention include those encoding the $V_H$ and $V_L$ sequences of the TIM-3 monoclonal antibody or the CDRs. Once DNA fragments encoding $V_H$ and $V_L$ segments are obtained, these DNA fragments can be further manipulated by standard recombinant DNA techniques, for example to convert the variable region genes to full-length antibody chain genes, to Fab fragment genes or to a scFv gene. In these manipulations, a $V_L$- or $V_H$-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the $V_H$-encoding DNA to another DNA molecule encoding heavy chain constant regions ($C_{H1}$, $C_{H2}$ and $C_{H3}$). The sequences of human heavy chain constant region genes are known in the art and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the $V_H$-encoding DNA can be operatively linked to another DNA molecule encoding only the heavy chain $C_{H1}$ constant region.

The isolated DNA encoding the $V_L$ region can be converted to a full-length light chain gene (as well as a Fab light chain gene) by operatively linking the $V_L$-encoding DNA to another DNA molecule encoding the light chain constant region, $C_L$. The sequences of human light chain constant region genes are known in the art and DNA fragments encompassing these regions can be obtained by standard PCR amplification. In preferred embodiments, the light chain constant region can be a kappa or lambda constant region.

To create a scFv gene, the $V_H$- and $V_L$-encoding DNA fragments are operatively linked to another fragment encoding a flexible linker, e.g., encoding the amino acid sequence (Gly4-Ser)3, such that the $V_H$ and $V_L$ sequences can be expressed as a contiguous single-chain protein, with the $V_L$ and $V_H$ regions joined by the flexible linker (see e.g., Bird et al., (1988) *Science* 242:423-426; Huston et al., (1988) *Proc. Natl. Acad. Sci. USA* 85:5879-5883; McCafferty et al. (1990) *Nature* 348:552-554).

Production of Monoclonal Antibodies of the Invention

Monoclonal antibodies (mAbs) of the present invention can be produced using the well-known somatic cell hybridization (hybridoma) technique of Kohler and Milstein (1975) *Nature* 256: 495. Other embodiments for producing monoclonal antibodies include viral or oncogenic transformation of B lymphocytes and phage display techniques. Chimeric or humanized antibodies are also well known in the art. See e.g., U.S. Pat. Nos. 4,816,567; 5,225,539; 5,530,101; 5,585,089; 5,693,762 and 6,180,370, the contents of which are specifically incorporated herein by reference in their entirety.

In a preferred embodiment, the antibodies of the invention are human monoclonal antibodies. Such human monoclonal antibodies directed against human TIM-3 can be generated using transgenic or transchromosomic mice carrying parts of the human immune system rather than the mouse system. These transgenic and transchromosomic mice include mice referred to herein as the HuMAb Mouse™ and KM Mouse™, respectively, and are collectively referred to herein as "human Ig mice."

The HuMAb Mouse™ (Medarex™, Inc.) contains human immunoglobulin gene miniloci that encode unrearranged human heavy (μ and γ) and κ light chain immunoglobulin sequences, together with targeted mutations that inactivate the endogenous μ and κ chain loci (see e.g., Lonberg et al. (1994) *Nature* 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal antibodies (Lonberg et al. (1994), supra; reviewed in Lonberg (1994) *Handbook of Experimental Pharmacology* 113: 49-101; Lonberg, N. and Huszar, D. (1995) *Intern. Rev. Immunol.* 13: 65-93, and Harding and Lonberg (1995) *Ann. N.Y. Acad. Sci.* 764:536-546). Preparation and use of the HuMAb Mouse™, and the genomic modifications carried by such mice, is further described in Taylor et al. (1992) *Nucleic Acids Research* 20:6287-6295; Chen et al. (1993) *International Immunology* 5: 647-656; Tuaillon et al. (1993) *Proc. Natl. Acad. Sci. USA* 90:3720-3724; Choi et al. (1993) *Nature Genetics* 4:117-123; Chen et al. (1993) *EMBO J.* 12: 821-830; Tuaillon et al. (1994) *J. Immunol.* 152:2912-2920; Taylor et al. (1994) *International Immunology* 6: 579-591; and Fishwild et al. (1996) *Nature Biotechnology* 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; 5,770,429; and 5,545,807; PCT Publication Nos. WO 92/03918; WO 93/12227; WO 94/25585; WO 97/13852; WO 98/24884; WO 99/45962 and WO 01/14424, the contents of which are incorporated herein by reference in their entirety.

In another embodiment, human antibodies of the invention can be raised using a mouse that carries human immunoglobulin sequences on transgenes and transchomosomes, such as a mouse that carries a human heavy chain transgene and a human light chain transchromosome. This mouse is referred to herein as a "KM Mouse™," and is described in detail in PCT Publication WO 02/43478. A modified form of this mouse, which further comprises a homozygous disruption of the endogenous FcγRIIB receptor gene, is also described in PCT Publication WO 02/43478 and referred to herein as a "KM/FCGR2D mouse." In addition, mice with either the HCo7 or HCo12 heavy chain transgenes or both can be used.

Additional transgenic animal embodiments include the Xenomouse (Abgenix, Inc., U.S. Pat. Nos. 5,939,598; 6,075,181; 6,114,598; 6,150,584 and 6,162,963). Further embodiments include "TC mice" (Tomizuka et al. (2000) *Proc. Natl. Acad. Sci. USA* 97:722-727) and cows carrying human heavy and light chain transchromosomes (Kuroiwa et al. (2002) *Nature Biotechnology* 20:889-894; PCT Publication WO 02/092812). The contents of these patents and publications are specifically incorporated herein by reference in their entirety.

In one embodiment, human monoclonal antibodies of the invention are prepared using phage display methods for screening libraries of human immunoglobulin genes. See, e.g. U.S. Pat. Nos. 5,223,409; 5,403,484; 5,571,698; 5,427,908; 5,580,717; 5,969,108; 6,172,197; 5,885,793; 6,521,404; 6,544,731; 6,555,313; 6,582,915; and 6,593,081, the contents of which are incorporated herein by reference in their entirety.

Human monoclonal antibodies of the invention can also be prepared using SCID mice into which human immune cells have been reconstituted such that a human antibody response can be generated upon immunization. See, e.g., U.S. Pat. Nos. 5,476,996 and 5,698,767, the contents of which are incorporated herein by reference in their entirety.

In another embodiment, human anti-TIM-3 antibodies are prepared using phage display where the phages comprise nucleic acids encoding antibodies generated in transgenic animals previously immunized with TIM-3. In a preferred embodiment, the transgenic animal is a HuMab, KM, or Kirin mouse. See, e.g. U.S. Pat. No. 6,794,132, the contents of which are incorporated herein by reference in its entirety.

Immunization of Human Ig Mice

In one embodiment of the invention, human Ig mice are immunized with a purified or enriched preparation of a TIM-3 antigen, recombinant TIM-3 protein, or cells expressing a TIM-3 protein. See, e.g., Lonberg et al. (1994), supra; Fishwild et al. (1996), supra; PCT Publications WO 98/24884 or WO 01/14424, the contents of which are incorporated herein by reference in their entirety. In a preferred embodiment, 6-16 week old mice are immunized with 5-50 μg of TIM-3 protein. Alternatively, a portion of TIM-3 fused to a non-TIM-3 polypeptide is used.

In one embodiment, the transgenic mice are immunized intraperitoneally (IP) or intravenously (IV) with TIM-3 antigen in complete Freund's adjuvant, followed by subsequent IP or IV immunizations with antigen in incomplete Freund's adjuvant. In other embodiments, adjuvants other than Freund's or whole cells in the absence of adjuvant are used. The plasma can be screened by ELISA and cells from mice with sufficient titers of anti-TIM-3 human immunoglobulin can be used for fusions.

Generation of Hybridomas Producing Human Monoclonal Antibodies of the Invention

To generate hybridomas producing human monoclonal antibodies of the invention, splenocytes and/or lymph node cells from immunized mice can be isolated and fused to an appropriate immortalized cell line, such as a mouse myeloma cell line. The resulting hybridomas can be screened for the production of antigen-specific antibodies. Generation of hybridomas is well-known in the art. See, e.g., Harlow and Lane (1988) *Antibodies, A Laboratory Manual*, Cold Spring Harbor Publications, New York.

Generation of Transfectomas Producing Monoclonal Antibodies of the Invention

Antibodies of the invention also can be produced in a host cell transfectoma using, for example, a combination of recombinant DNA techniques and gene transfection methods as is well known in the art (e.g., Morrison, S. (1985) *Science* 229:1202). In one embodiment, DNA encoding partial or full-length light and heavy chains obtained by standard molecular biology techniques is inserted into one or more expression vectors such that the genes are operatively linked to transcriptional and translational regulatory sequences. In this context, the term "operatively linked" is intended to mean that an antibody gene is ligated into a vector such that transcriptional and translational control sequences within the vector serve their intended function of regulating the transcription and translation of the antibody gene.

The term "regulatory sequence" is intended to include promoters, enhancers and other expression control elements (e.g., polyadenylation signals) that control the transcription or translation of the antibody chain genes. Such regulatory sequences are described, e.g., in Goeddel (Gene Expression Technology. Methods in Enzymology 185, Academic Press, San Diego, Calif. (1990)). Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, e.g., the adenovirus major late promoter (AdMLP) and polyoma. Alternatively, nonviral regulatory sequences can be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe et al. (1988) *Mol. Cell. Biol.* 8:466-472). The expression vector and expression control sequences are chosen to be compatible with the expression host cell used.

The antibody light chain gene and the antibody heavy chain gene can be inserted into the same or separate expression vectors. In preferred embodiments, the variable regions are used to create full-length antibody genes of any antibody isotype by inserting them into expression vectors already encoding heavy chain constant and light chain constant regions of the desired isotype such that the $V_H$ segment is operatively linked to the CH segment(s) within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes and regulatory sequences, the recombinant expression vectors of the invention can carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399, 216; 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody.

Preferred mammalian host cells for expressing the recombinant antibodies of the invention include Chinese Hamster Ovary (CHO cells) (including dhfr- CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *J. Mol. Biol.* 159:601-621), NSO myeloma cells, COS cells and SP2 cells. In particular, for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Immunoconjugates

Antibodies of the invention can be conjugated to a therapeutic agent to form an immunoconjugate such as an antibody-drug conjugate (ADC). Suitable therapeutic agents include antimetabolites, alkylating agents, DNA minor groove binders, DNA intercalators, DNA crosslinkers, histone deacetylase inhibitors, nuclear export inhibitors, proteasome inhibitors, topoisomerase I or II inhibitors, heat shock protein inhibitors, tyrosine kinase inhibitors, antibiotics, and anti-mitotic agents. In the ADC, the antibody and therapeutic agent preferably are conjugated via a linker cleavable such as a peptidyl, disulfide, or hydrazone linker. More preferably, the linker is a peptidyl linker such as Val-Cit, Ala-Val, Val-Ala-Val, Lys-Lys, Pro-Val-Gly-Val-Val, Ala-Asn-Val, Val-Leu-Lys, Ala-Ala-Asn, Cit-Cit, Val-Lys, Lys, Cit, Ser, or Glu. The ADCs can be prepared as described in U.S. Pat. Nos. 7,087,600; 6,989,452; and 7,129, 261; PCT Publications WO 02/096910; WO 07/038,658; WO 07/051,081; WO 07/059,404; WO 08/083,312; and WO 08/103,693; U.S. Patent Publications 20060024317; 20060004081; and 20060247295; the disclosures of which are incorporated herein by reference.

Bispecific Molecules

In another aspect, the present disclosure features bispecific molecules comprising one or more antibodies of the invention linked to at least one other functional molecule, e.g., another peptide or protein (e.g., another antibody or ligand for a receptor) to generate a bispecific molecule that binds to at least two different binding sites or target molecules. Thus, as used herein, "bispecific molecule" includes molecules that have three or more specificities.

In an embodiment, a bispecific molecule has, in addition to an anti-Fc binding specificity and an anti-TIM-3 binding specificity, a third specificity. The third specificity can be for an anti-enhancement factor (EF), e.g., a molecule that binds to a surface protein involved in cytotoxic activity and thereby increases the immune response against the target cell. For example, the anti-enhancement factor can bind a cytotoxic T-cell (e.g. via CD2, CD3, CD8, CD28, CD4, CD40, or ICAM-1) or other immune cell, resulting in an increased immune response against the target cell.

Bispecific molecules can come in many different formats and sizes. At one end of the size spectrum, a bispecific molecule retains the traditional antibody format, except that, instead of having two binding arms of identical specificity, it has two binding arms each having a different specificity. At the other extreme are bispecific molecules consisting of two single-chain antibody fragments (scFv's) linked by a peptide chain, a so-called Bs(scFv) 2 construct. Intermediate-sized bispecific molecules include two different F(ab) fragments linked by a peptidyl linker. Bispecific molecules of these and other formats can be prepared by genetic engineering, somatic hybridization, or chemical methods. See, e.g., Kufer et al, cited supra; Cao and Suresh, Bioconjugate Chemistry, 9 (6), 635-644 (1998); and van Spriel et al., *Immunology Today*, 21 (8), 391-397 (2000), and the references cited therein.

Pharmaceutical Compositions

In another aspect, the present disclosure provides a pharmaceutical composition comprising one or more antibodies of the present invention formulated together with a pharmaceutically acceptable carrier. The composition may optionally contain one or more additional pharmaceutically active ingredients, such as another antibody or a drug. The pharmaceutical compositions of the invention also can be administered in a combination therapy with, for example, another immune-stimulatory agent, anti-cancer agent, an anti-viral agent, or a vaccine, such that the anti-TIM-3 antibody enhances the immune response against the vaccine.

The pharmaceutical composition can comprise any number of excipients. Excipients that can be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients is taught in Gennaro, ed., *Remington: The Science and Practice of Pharmacy*, 20th Ed. (Lippincott Williams & Wilkins 2003), the disclosure of which is incorporated herein by reference.

Preferably, the pharmaceutical composition is suitable for intravenous, intramuscular, subcutaneous, parenteral, spinal or epidermal administration (e.g., by injection or infusion). Depending on the route of administration, the active compound can be coated in a material to protect it from the action of acids and other natural conditions that may inactivate it. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, an antibody of the invention can be administered via a non-parenteral route, such as a topical, epidermal or mucosal route of administration, e.g., intranasally, orally, vaginally, rectally, sublingually or topically.

Pharmaceutical compositions can be in the form of sterile aqueous solutions or dispersions. They can also be formulated in a microemulsion, liposome, or other ordered structure suitable to high drug concentration.

The amount of active ingredient which can be combined with a carrier material to produce a single dosage form will vary depending upon the subject being treated and the particular mode of administration and will generally be that amount of the composition which produces a therapeutic effect. Generally, out of one hundred percent, this amount will range from about 0.01% to about ninety-nine percent of active ingredient, preferably from about 0.1% to about 70%, most preferably from about 1% to about 30% of active ingredient in combination with a pharmaceutically acceptable carrier.

Dosage regimens are adjusted to provide the optimum desired response (e.g., a therapeutic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. Alternatively, antibody can be administered as a sustained release formulation, in which case less frequent administration is required.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an anti-TIM-3 antibody of the invention include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks. In some methods, dosage is adjusted to achieve a plasma antibody concentration of about 1-1000 μg/ml and in some methods about 25-300 μg/ml.

A "therapeutically effective dosage" of an anti-TIM-3 antibody of the invention preferably results in a decrease in severity of disease symptoms, an increase in frequency and duration of disease symptom-free periods, or a prevention of impairment or disability due to the disease affliction. For example, for the treatment of tumor-bearing subjects, a "therapeutically effective dosage" preferably inhibits tumor growth by at least about 20%, more preferably by at least about 40%, even more preferably by at least about 60%, and still more preferably by at least about 80% relative to untreated subjects. A therapeutically effective amount of a therapeutic compound can decrease tumor size, or otherwise ameliorate symptoms in a subject, which is typically a human or can be another mammal.

The pharmaceutical composition can be a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. See, e.g., Sustained and Controlled Release Drug Delivery Systems, J. R. Robinson, ed., Marcel Dekker, Inc., New York, 1978.

Therapeutic compositions can be administered via medical devices such as (1) needleless hypodermic injection devices (e.g., U.S. Pat. Nos. 5,399,163; 5,383,851; 5,312,335; 5,064,413; 4,941,880; 4,790,824; and 4,596,556); (2) micro-infusion pumps (U.S. Pat. No. 4,487,603); (3) transdermal devices (U.S. Pat. No. 4,486,194); (4) infusion apparati (U.S. Pat. Nos. 4,447,233 and 4,447,224); and (5) osmotic devices (U.S. Pat. Nos. 4,439,196 and 4,475,196); the disclosures of which are incorporated herein by reference.

In certain embodiments, the mouse monoclonal antibodies of the invention can be formulated to ensure proper distribution in vivo. For example, to ensure that the therapeutic compounds of the invention cross the blood-brain barrier, they can be formulated in liposomes, which may additionally comprise targeting moieties to enhance selective transport to specific cells or organs. See, e.g. U.S. Pat. Nos. 4,522,811; 5,374,548; 5,416,016; and 5,399,331; V. V. Ranade (1989) *J. Clin. Pharmacol.* 29:685; Umezawa et al., (1988) *Biochem. Biophys. Res. Commun.* 153:1038; Bloeman et al. (1995) *FEBS Lett.* 357:140; M. Owais et al. (1995) *Antimicrob. Agents Chemother.* 39:180; Briscoe et al. (1995) *Am. J. Physiol.* 1233:134; Schreier et al. (1994) *J. Biol. Chem.* 269:9090; Keinanen and Laukkanen (1994) *FEBS Lett.* 346:123; and Killion and Fidler (1994) *Immunomethods* 4:273.

Uses and Methods of the Invention

Antibodies (compositions, bispecifics, and immunoconjugates) of the present invention have numerous in vitro and in vivo utilities involving, for example, enhancement of immune responses by blockade of TIM-3. The antibodies can be administered to cells in culture, in vitro or ex vivo, or to human subjects, e.g., in vivo, to enhance immunity in a variety of situations. Accordingly, in one aspect, the invention provides a method of modifying an immune response in a subject comprising administering to the subject the antibody, or antigen-binding portion thereof, of the invention such that the immune response in the subject is modified. Preferably, the response is enhanced, stimulated or up-regulated.

Preferred subjects include human patients in need of enhancement of an immune response. The methods are particularly suitable for treating human patients having a disorder that can be treated by augmenting an immune response (e.g., the T-cell mediated immune response). In a particular embodiment, the methods are particularly suitable for treatment of cancer in vivo. To achieve antigen-specific enhancement of immunity, the anti-TIM-3 antibodies can be administered together with an antigen of interest or the antigen may already be present in the subject to be treated (e.g., a tumor-bearing or virus-bearing subject). When antibodies to TIM-3 are administered together with another agent, the two can be administered in either order or simultaneously.

Given the ability of anti-TIM-3 antibodies of the invention to inhibit the binding of TIM-3 to galectin-9 or PtdSer molecules and to activate antigen specific CD4+ or CD8+ T cells, the invention also provides in vitro and in vivo methods of using the antibodies to enhance or upregulate antigen-specific T cell responses. For example, the invention provides a method of enhancing an antigen-specific T cell response comprising contacting said T cell with an antibody of the invention, such that an antigen-specific T cell response is enhanced or upregulated.

The invention also provides method for enhancing an immune response (e.g., an antigen-specific T cell response) in a subject comprising administering an antibody of the invention to the subject such that an immune response (e.g., an antigen-specific T cell response) in the subject is enhanced. In a preferred embodiment, the subject is a tumor-bearing subject and an immune response against the tumor is enhanced. In another preferred embodiment, the subject is a virus-bearing subject and an immune response against the virus is enhanced.

In another embodiment, the invention provides methods for inhibiting growth of tumor cells in a subject comprising administering to the subject an antibody of the invention such that growth of the tumor is inhibited in the subject. In yet another embodiment, the invention provides methods for treating a viral infection in a subject comprising administering to the subject an antibody of the invention such that the viral infection is treated in the subject.

These and other methods of the invention are discussed in further detail below.

Cancer

Blockade of TIM-3 by antibodies can enhance the immune response to cancerous cells in the patient. In one aspect, the present invention relates to treatment of a subject in vivo using an anti-TIM-3 antibody such that growth of cancerous tumors is inhibited. An anti-TIM-3 antibody can be used alone to inhibit the growth of cancerous tumors. Alternatively, an anti-TIM-3 antibody can be used in conjunction with other immunogenic agents, standard cancer treatments, or other antibodies, as described below.

Accordingly, in one embodiment, the invention provides a method of inhibiting growth of tumor cells in a subject, comprising administering to the subject a therapeutically effective amount of an anti-TIM-3 antibody, or antigen-binding portion thereof. Preferably, the antibody is a chimeric, human or humanized anti-TIM-3 antibody.

Preferred cancers whose growth may be inhibited using the antibodies of the invention include cancers typically responsive to immunotherapy.

Combination Therapy

In another aspect, the invention provides methods of combination therapy in which an anti-TIM-3 antibody (or antigen-binding portion thereof) of the present invention is co-administered with one or more additional antibodies that are effective in stimulating immune responses to thereby further enhance, stimulate or upregulate immune responses in a subject. In one embodiment, the invention provides a method for stimulating an immune response in a subject comprising administering to the subject an anti-TIM-3 antibody and one or more additional immune-stimulatory antibodies, such as an anti-LAG-3 antibody, an anti-PD-1 antibody and/or an anti-CTLA-4 antibody, such that an immune response is stimulated in the subject, for example to inhibit tumor growth or to stimulate an anti-viral response.

In another embodiment, the invention provides a method for treating a hyperproliferative disease (e.g., cancer), comprising administering an anti-TIM-3 antibody and another antibody such as anti-LAG-3 antibody, an anti-PD-1 antibody and/or an anti-CTLA-4 antibody to a subject.

In certain embodiments, the combination of therapeutic antibodies discussed herein can be administered concurrently as a single composition in a pharmaceutically acceptable carrier, or concurrently as separate compositions with each antibody in a pharmaceutically acceptable carrier.

Optionally, the combination of anti-TIM-3 and one or more additional antibodies (e.g., anti-CTLA-4 and/or anti-LAG-3 and/or anti-PD-1 antibodies) can be further combined with an immunogenic agent, such as cancerous cells, purified tumor antigens (including recombinant proteins, peptides, and carbohydrate molecules), cells, and cells transfected with genes encoding immune stimulating cytokines (He et al. (2004) J. Immunol. 173:4919-28). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF. A combined TIM-3 and CTLA-4 and/or LAG-3 and/or PD-1 blockade can be further combined with a vaccination protocol, such as any of the vaccination protocols discussed in detail above with respect to monotherapy with anti-TIM-3 antibodies.

A combined TIM-3 and CTLA-4 and/or LAG-3 and/or PD-1 blockade can also be further combined with standard cancer treatments. For example, a combined TIM-3 and CTLA-4 and/or LAG-3 and/or PD-1 blockade can be effectively combined with chemotherapeutic regimes. In these instances, it is possible to reduce the dose of other chemotherapeutic reagent administered with the combination of the instant disclosure (Mokyr et al. (1998) Cancer Research 58: 5301-5304). An example of such a combination is a combination of anti-TIM-3 and anti-CTLA-4 antibodies and/or anti-LAG-3 antibodies and/or anti-PD-1 antibodies further in combination with decarbazine for the treatment of melanoma. Another example is a combination of anti-TIM-3 and anti-CTLA-4 antibodies and/or anti-LAG-3 antibodies and/or anti-PD-1 antibodies further in combination with interleukin-2 (IL-2) for the treatment of melanoma. The scientific rationale behind the combined use of TIM-3 and CTLA-4 and/or LAG-3 and/or PD-1 blockade with chemotherapy is that cell death, which is a consequence of the cytotoxic action of most chemotherapeutic compounds, should result in increased levels of tumor antigen in the antigen presentation pathway. Other combination therapies that may result in synergy with a combined TIM-3 and CTLA-4 and/or LAG-3 and/or PD-1 blockade through cell death include radiation, surgery, or hormone deprivation. Each of these protocols creates a source of tumor antigen in the host. Angiogenesis inhibitors can also be combined with a combined TIM-3 and CTLA-4 and/or LAG-3 and/or PD-1 blockade. Inhibition of angiogenesis leads to tumor cell death, which can be a source of tumor antigen fed into host antigen presentation pathways.

The present disclosure is further illustrated by the following examples, which should not be construed as further limiting. The contents of all figures and all references, Genbank sequences, patents and published patent applications cited throughout this application are expressly incorporated herein by reference.

EXAMPLES

Example 1 Phage Panning, Screening and Affinity Maturation

Phage Library

An antibody single chain phage display library was created by cloning a repertoire of light chain variable regions ($V_L$) and heavy chain variable regions ($V_H$). The heavy and light chain repertoires were created by PCR amplification from human lymphocytes mainly collected from peripheral. The $V_L$ repertoire and $V_H$ repertoire were mixed and underwent PCR with overlapping primers. The final format of the antibody was a single chain Fv (scFv) with $V_H$ and $V_L$ fragments joined by a flexible linker peptide (GGGGSGGGGSGGGGS (SEQ ID NO: 51)).

Phage Library Panning Against Human TIM-3

Selection of phage particles displaying specific scFv fragments was performed on Immuno 96 MicroWell™ Plates (Nunc, Denmark). First, 50 μg/ml of TIM-3 recombinant protein (AcroBiosystems, cat #TM3-H5229) in phosphate-buffered saline (PBS) was coated on the plates overnight at 4° C. Following blocking with 2% (w/v) milk powder in PBS (2% MPBS), a library containing about 1011 phage particles were added and the plate was incubated for 2 hours at room temperature (RT; 25-28° C.). Non-bound phages were eliminated by washing 10-20 times with PBS containing 0.1% Tween 20 (PBS-T), followed by 10-20 times washing with PBS. The bound phages were eluted by incubation with 50 μl of 1 μg/μl trypsin for 10 min, followed by 50 μl of 50 mM glycine-HCl pH 2.0 (immediately neutralized with 50 μl of 200 mM $Na_2HPO_4$, pH7.5 after 10 min). Four rounds of panning were performed.

Phage Screening

From the third and fourth round of panning output, phages were picked up and tested for human TIM-3 binding, human TIM-3 (AcroBiosystems, cat #TM3-H5229) were coated on 96-well plate at 0.1 μg/mL, single clone phages were added into plates, unbounded phage were washed away and bound were detected by anti-M13 secondary antibody (Abcam, cat #ab50370).

ELISA positive clones were sequenced, from which 10 unique sequences were identified including clone TIM3-6, TIM3-4G7, and TIM3-11. The amino acid sequence ID numbers of heavy/light chain variable region of anti-TIM-3 antibody TIM3-6, TIM3-4G7 and TIM3-11 were summarized in Table 1.

Affinity Maturation

To improve the binding affinity of TIM3-6, two phage libraries for $V_H$ and $V_L$ were constructed for panning. After 4 rounds of panning, variants were tested for positive binding to human TIM-3 (AcroBiosystems, cat #TM3-H5229) by ELISA screening. Off-rate ranking of positive variants was determined by Octet Red 96 (Fortebio). Clones with improved off-rate were picked and converted to full length IgG for analysis. The amino acid sequence ID numbers of anti-TIM-3 antibody TIM3-6.10, TIM3-6.11 and TIM3-6.12 were summarized in Table 1.

Nucleotide sequences encoding the heavy chain and light chain of anti-TIM-3 antibodies were inserted into the expression vector pcDNA3.1 (Invitrogen). Vectors were co-transfected into CHO-S cells using ExpiCHO™ Expression System (ThermoFisher) according to manufacturer's instructions. The transfected cells were cultured in ExpiCHO™ Expression Medium for 12 days, and then culture supernatants were harvested and sent for purification with Protein A affinity chromatography (GE healthcare).

Example 2 Physical and Chemical Analysis

Antibody TIM3-6 was tested in Size Exclusion Chromatography. In particular, 20 μg of the sample was injected on a TSK G3000SWXL column using 100 mM sodium phosphate +100 mM $Na_2SO_4$, pH 7.0, as running buffer. The run time was 30 min. All measurements were performed on Agilent 1220 HPLC. Data was analyzed using OpenLAB software.

The main peak of antibody TIM3-6 was above 95% in SEC, suggesting high purity and integrity of the purified antibody.

Example 3 Anti-TIM-3 Antibodies Bound to Human TIM-3 Specifically

An ELISA assay was used for determination of the relative binding activity of antibodies to recombinant human TIM-3.

Human TIM-3 protein (Acrobiosystems, Cat #TM3-H5229) in carbonate buffer (pH 9.6, 1.59 g sodium carbonate and 2.93 g sodium bicarbonate dissolved in 1 L water) was immobilized onto 96-well plates at 1 μg/mL by incubation overnight at 4° C. The plates were then blocked with 1% BSA in PBS for one hour at 37° C. After blocking, the plates were washed three times with PBST (PBS containing 0.05% Tween20). Serially diluted anti-TIM-3 antibodies TIM3-6.12, TIM3-6, TIM3-11, and TIM3-4G7, human IgG control (prepared according to US20190016800A1, with the amino acid sequence set forth in SEQ ID NO: 52), and ABTIM3 analog (used as the reference antibody, prepared according to US 2015/0218274A1, with amino acid sequences of heavy chain and light chain set forth in SEQ ID NOs: 53 and 54) in binding buffer (PBS containing 0.05% Tween20 and 0.5% BSA) were respectively incubated with the immobilized proteins for one hour at 37° C. After binding, the plates were washed three times with PBST, incubated for one hour at 37° C. with peroxidase-labeled donkey anti-human IgG (Jackson Immuno Research) diluted 1/15,000 in binding buffer, washed again, developed with TMB and stopped with 1M $H_2SO_4$.

The absorbance at 450 nm-620 nm was determined. The $EC_{50}$ and representative binding curves for the clones binding to human TIM-3 were shown in FIG. 1.

The result indicated that anti-TIM-3 antibodies bound to human TIM-3 specifically, wherein the binding activity of antibody TIM3-6.12 was comparable to that of the ABTIM3 analog.

Example 4 Affinity of Anti-TIM-3 Antibodies

The kinetic binding activity of anti-TIM-3 antibodies to human TIM-3 (Acrobiosystems, Cat #TM3-H5229) was measured by surface plasmon resonance using a Biacore® T200 system (Biacore, GE Healthcare).

Approximately 6800 RU of Anti-Human IgG (Fc) antibody (GE Catalog #BR-1008-39) was immobilized via amine coupling chemistry onto a CM5 sensor chip. Antibodies (TIM3-6.10, TIM3-6.11, TIM3-6.12) were injected over the surface of the immobilized goat anti-human IgG antibody. HBS-EP+ buffer was used as the running buffer. Varying concentrations of human TIM-3 protein, ranging from 1.56 nM to 50 nM, were injected over the antibody surfaces. Following each injection cycle, the CM5 chip surface was regenerated using injection of 3M magnesium chloride solution. Background subtraction binding sensorgrams were used for analyzing the rate of association $K_a$ and dissociation $K_d$, and the equilibrium dissociation constant $K_D$. The resulting data sets were fitted with a 1:1 *Langmuir* Binding Model using the Biacore T200 evaluation software.

Table 2 below summarized the affinities of the anti-TIM-3 antibodies to recombinant human TIM-3.

TABLE 2

Affinities of anti-TIM-3 antibodies to recombinant human TIM-3

| Antibody # | Ka ($M^{-1}S^{-1}$) | Kd ($S^{-1}$) | $K_D$ (M) |
|---|---|---|---|
| TIM3-6.10 | 2.02E+05 | 4.15E−04 | 2.05E−09 |
| TIM3-6.11 | 2.30E+05 | 3.44E−04 | 1.50E−09 |
| TIM3-6.12 | 2.23E+05 | 3.70E−04 | 1.66E−09 |

The results showed that the three antibodies had similar affinity to recombinant human TIM-3, with antibody TIM3-6.11 had the highest affinity.

Example 5 Anti-TIM-3 Antibodies Did not Cross React with Human TIM-1

An ELISA assay was used for determination of the relative binding activity of antibodies to human TIM-1.

Human TIM-1 (Sino biological, Cat #11051-HNCH) was immobilized onto 96-well plates by incubation overnight at 4° C. Nonspecific binding sites were blocked with 1% BSA in PBS for one hour at 37° C. After blocking, the plates were washed three times with PBST (PBS containing 0.05% Tween20). Serially diluted anti-TIM-3 antibody TIM3-6, the ABTIM3 analog, and human IgG control were prepared in binding buffer (PBS containing 0.05% Tween20 and 0.5% BSA) and incubated with the immobilized proteins for one hour at 37° C. After binding, the plates were washed three times with PBST, incubated for one hour at 37° C. with peroxidase-labeled donkey anti-human IgG (Jackson Immuno Research) diluted 1/15,000 in binding buffer, washed again, developed with TMB and stopped with 1M $H_2SO_4$.

The absorbance at 450 nm-620 nm was determined. The result suggested that that TIM3-6 did not cross-react with human TIM-1.

Example 6 Anti-TIM-3 Antibodies Did not Cross React with Human TIM-4

An ELISA assay was used for determination of the relative binding activity of anti-TIM-3 antibodies to human TIM-4.

Human TIM-4 (Sino biological, Cat #12161-H08H) was immobilized onto 96-well plates by incubation overnight at 4° C. Nonspecific binding sites were blocked with 1% BSA in PBS for one hour at 37° C. After blocking, the plates were washed three times with PBST (PBS containing 0.05% Tween20). Serially diluted anti-TIM-3 antibody TIM3-6, the ABTIM3 analog, and human IgG control were prepared in binding buffer (PBS containing 0.05% Tween20 and 0.5% BSA) and incubated with the immobilized proteins for one hour at 37° C. After binding, the plates were washed three times with PBST, incubated for one hour at 37° C. with peroxidase-labeled donkey anti-human IgG (Jackson Immuno Research) diluted 1/15,000 in binding buffer, washed again, developed with TMB and stopped with 1M $H_2SO_4$.

The absorbance at 450 nm-620 nm was determined. The result suggested that TIM3-6 did not bind to human TIM-4.

Example 7 Anti-TIM-3 Antibodies Blocked Interaction of Galectin-9 with TIM-3

To assess the inhibitory effect of the anti-TIM-3 antibodies on human TIM-3/galectin-9 interaction, an HTRF blocking assay was performed using a commercially available kit (Cisbio, cat #63ADK000CTLPEB) in which Eu3+ cryptate labeled TIM3 reacted with Tag-Gal9.

Figure 2:
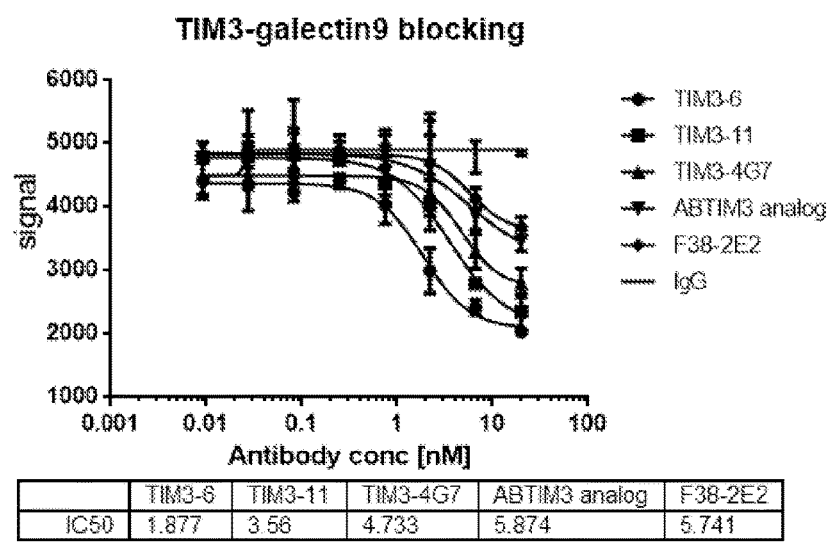
FIG. 2 shows the blocking activity of anti-TIM-3 antibodies of the invention on human TIM-3-galectin-9 interaction.

To test the antibodies in this assay, serially diluted anti-TIM-3 antibody TIM3-6, TIM3-11, TIM3-4G7, F38-2E2 (ebioscience, cat #16-3109-85), the ABTIM3 analog, and human IgG control were added to Tim3-EuK protein/Tag-Gal9 protein mixture, respectively. The resultant mixture was incubated for 1 h at room temperature and then the fluorescence emission was read. The $IC_{50}$ values and representative curves for blocking the galectin-9 and TIM-3 interaction were shown in FIG. 2.

The result indicated that anti-TIM-3 antibodies TIM3-6, TIM3-11 and TIM3-4G7 blocked interaction between galectin9 and TIM-3 at lower $IC_{50}$ values than the ABTIM3 analog and F38-2E2, suggesting their better blocking activities. Antibody TIM3-6 had the best blocking activity.

Example 8 Anti-TIM-3 Antibodies Bound to Cell Surface TIM-3 Expressed by CHO-K1-TIM-3

Anti-TIM-3 antibodies were tested for their binding ability to human TIM-3 stably expressed on CHO-K1 cells. A Chinese hamster ovary epithelial CHO-K1 cell line (ATCC, cat #CCL-61) was maintained in F-12K medium containing 10% FBS in a humidified incubator with 5% $CO_2$ at 37° C. Polyethylenimine (MW25K, 23966-2, Polyscience) was diluted to 1 mg/mL, and added to and incubated with pcDNA3.1 vector containing TIM-3 cDNA (NP_116171.3) at 37° C. for 10 mins. The mixture was added to and incubated with cell culture for 3 hrs for DNA transfection.

Figure 3:
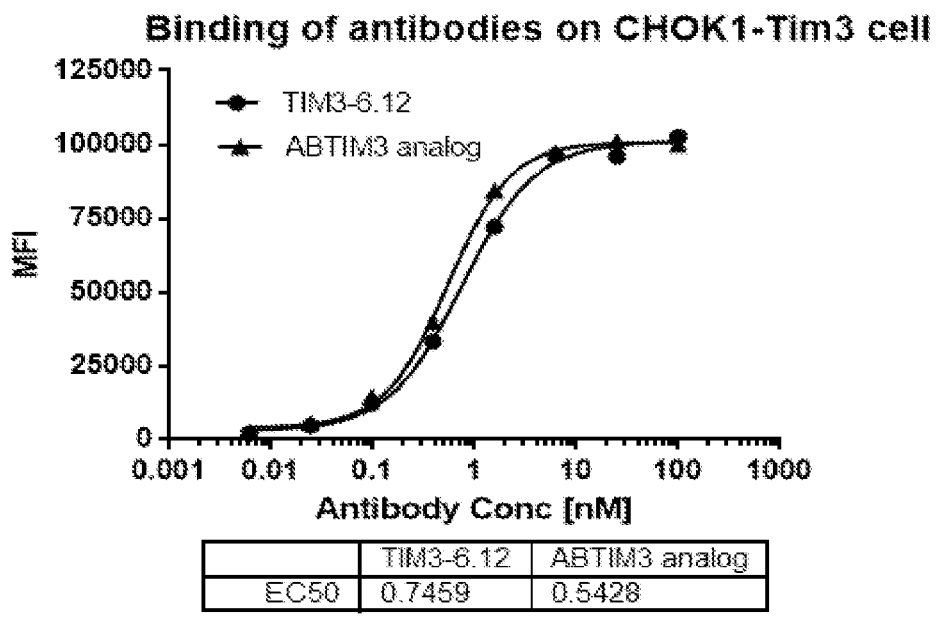
FIG. 3 shows the binding activity of anti-TIM-3 antibodies of the invention to TIM-3 expressed on CHO-K1-TIM-3 cells.

The anti-TIM-3 antibodies were serially diluted in PBS buffer with 0.5% BSA. The antibodies were added to and incubated with CHO-K1-TIM-3 cells at 4° C. for 30 min. The cells were pelleted (3 minutes, 600×g), washed once using PBS buffer with 0.5% BSA and re-pelleted. Then, the cells were incubated with a PE conjugated AffiniPure Goat Anti-human IgG, Fc γ Fragment Specific (Jackson ImmunoResearch Cat #109-116-098) diluted at 1:100 at 4° C. for 30 mins. Cells were washed twice as described above, resuspended in PBS buffer. The cells were then sent to the BD Accuri C5 flow cytometer (BD Bioscience) for binding activity analysis. The $EC_{50}$ values were calculated. Representative curves for binding of the antibodies to TIM-3 were shown in FIG. 3.

The result indicated that TIM3-6.12 bound to human TIM-3 stably expressed on CHO-K1 cells specifically, and its binding activity was comparable to that of the ABTIM3 analog.

Example 9 Anti-TIM-3 Antibodies Induced Human T Cell to Release IL-2

The functional activity of the anti-TIM3 antibodies on primary T cells was assessed using human PBMC cultures stimulated by superantigen SEB.

Human PBMCs from healthy donors were stimulated with SEB (Toxin Technology, cat #BT202) for 48 hours. Serially diluted antibody TIM3-6.12, F38-2E2 (ebioscience, cat #16-3109-85) and human IgG control were respectively added to and incubated with PBMC cultures for 3 days. Then, the IL-2 level in the supernatants was measured using the Human IL-2 DuoSet ELISA Kit (R&D, cat #DY202).

Figure 4:
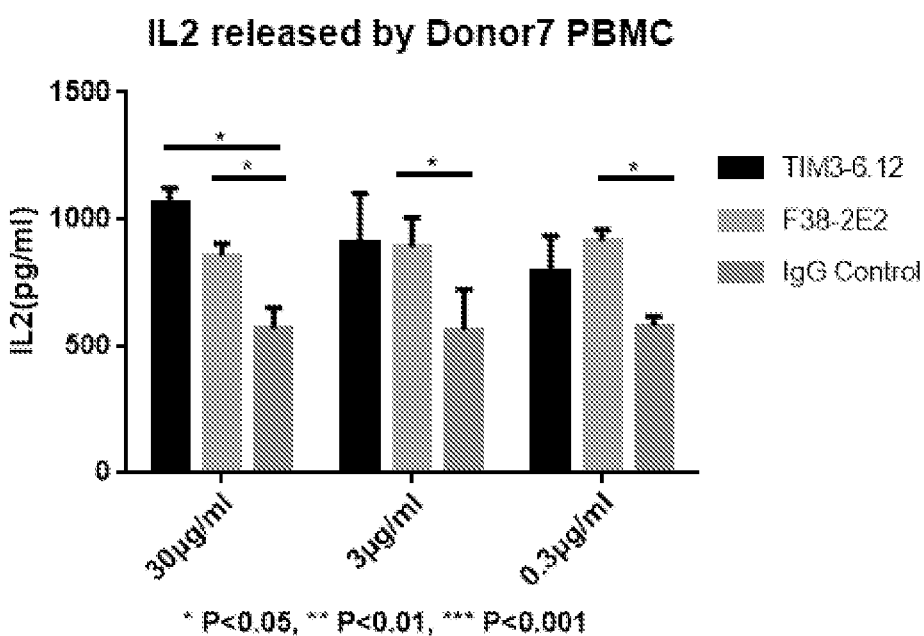
FIG. 4 shows IL-2 released by PBMCs treated with SEB followed by anti-TIM-3 antibodies of the invention.

As shown in FIG. 4, antibody TIM3-6.12 at 30 μg/ml induced T cells to release IL-2.

Example 10 Anti-TIM-3 Antibodies Blocked Interaction of TIM-3 with Phosphatidylserine Phosphatidylserine-TIM-3 interaction blocking assay was performed as follows.

Briefly, Jurkat T cells (CBTCCCAS, Clone E6-1) were incubated with 1 μg/mL anti-human CD95 (Fas) antibody (Clone E059.1, Biogems, Cat #08011-25-500) for 16 h. When Jurkat T cell were induced to undergo apoptosis, phosphatidylserines flipped to the extracellular surface of the cell, to which TIM-3 might bind.

Human TIM-3-mFc protein (amino acid sequence set forth in SEQ ID NO: 55) of 25 μl (40 μm/ml) was mixed and incubated with 25111 of serially diluted antibodies (started at 1 μm/mL) in Annexin V binding buffer (Biolegend Cat 422201) at room temperature (RT) for 20 minutes. Then, the mixture was added to 2×10$^5$ Jurkat T cells in 50 μl binding buffer (PBS containing 0.5% BSA). After incubation at 4° C. for 40 minutes, the cells were pelleted (3 minutes, 600×g), washed once using binding buffer with 0.5% BSA and re-pelleted. The cells were then added with PE conjugated AffiniPure Goat Anti-Mouse IgG (subclasses 1+2a+2b+3), Fcγ Fragment Specific (Jackson ImmunoResearch, Cat #115-115-164) diluted at 1:100, and were analyzed with the BD Accuri C5 flow cytometer.

Figure 5:
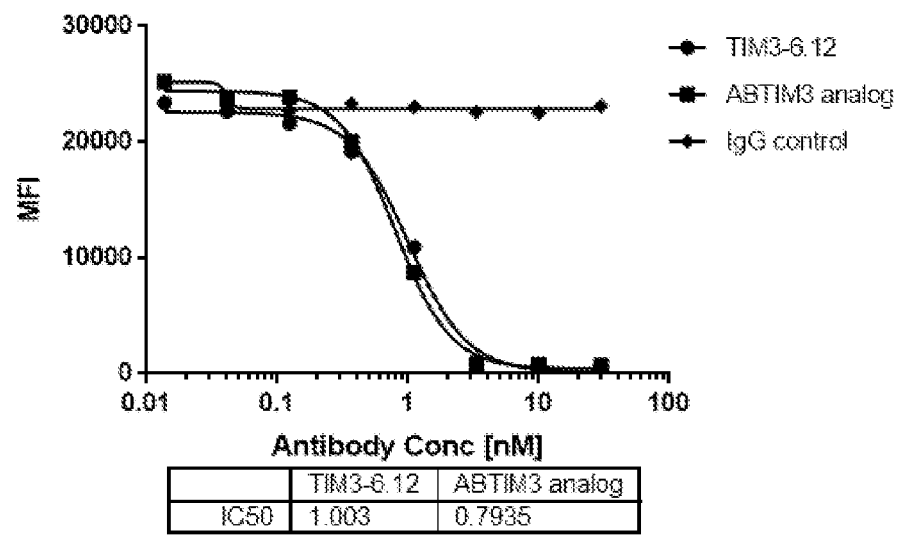
FIG. 5 shows the blocking activity of anti-TIM-3 antibodies of the invention on TIM-3-phosphatidylserine interaction.

As shown in FIG. 5, the anti-TIM-3 antibody TIM3-6.12 blocked TIM-3-phosphatidylserine interaction with a similar $IC_{50}$ value to the ABTIM3 analog.

Example 11 Internalization of Anti-TIM-3 Antibody by CHO-K1-TIM-3 Cells

The anti-TIM-3 antibody was first labeled with pHAb Amine Reactive Dye (Promega, G9845), a pH sensitive dye which became fluorescent when pH value was less than 7.0, according to manufacturer's instructions.

CHO-K1-TIM-3 as generated in Example 8 were cultured in DMEM/F12 medium containing 10% fetal bovine serum (Gibco). Cells at the log phase were collected, added with 50 μl of 20 μg/ml dye labeled antibodies, and incubated for 2 hrs, 6 hrs or 24 hrs at 37° C. Then, the cells were sent for analysis with the BD Accuri C5 flow cytometer.

Figure 6:
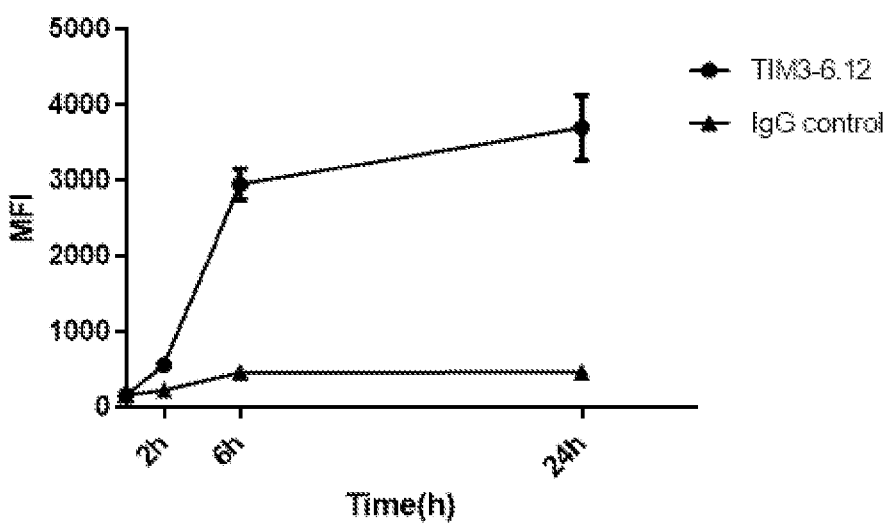
FIG. 6 shows internalization of anti-TIM-3 antibodies of the invention by CHO-K1-TIM-3 cells.

As shown in FIG. 6, fluorescent signals were detected, indicating that the anti-TIM-3 antibody TIM3-6.12 had probably been internalized into intracellular endosomes (pH 6.0-6.5) and lysosomes (pH 4.5-5.5).

Example 12 Anti-TIM-3 Antibodies Did not Bind to C1q

C1q binding was the first step of Complement-Dependent Cytotoxicity (CDC). To test the antibody's binding activity to C1q, an ELISA binding assay was performed.

Briefly, 96-well polystyrene ELISA plates were coated with antibody TIM3-6.12, a Rituximab analog (used as the positive control, prepared according to U.S. Pat. No. 5,736,137, having SEQ ID NOs: 56 and 57 as the heavy chain and light chain amino acid sequences), human IgG control at concentrations ranging from 60-0.94 μg/mL in PBS. After overnight incubation at 4° C., the plates were washed three times with PBST and then blocked with 200 μl of PBS containing 1% BSA for one hour at 37° C. The plates were washed 3 times with PBST and then 0.05 μg/well of C1q (Calbiochem, Cat #204876), diluted in PBS containing 0.05% Tween20 and 0.5% BSA, was added. After incubation for one hour at 37° C., the plates were washed three times with PBST and 50 μL of Anti-C1q antibody-HRP (1:400, abcam, cat #ab46191) was added to each well. The plates were incubated for one hour at room temperature and then washed three times with PBST. 100 μL of 3,3',5,5'-Tetramethylbenzidine (TMB: Thermo Cat #34028), a substrate of HRP, was then added to each well and the plates were incubated at room temperature for 20 minutes. The reaction was stopped with 1M $H_2SO_4$ and the absorbance was measured at 450 nM using a microplate reader.

Figure 7:
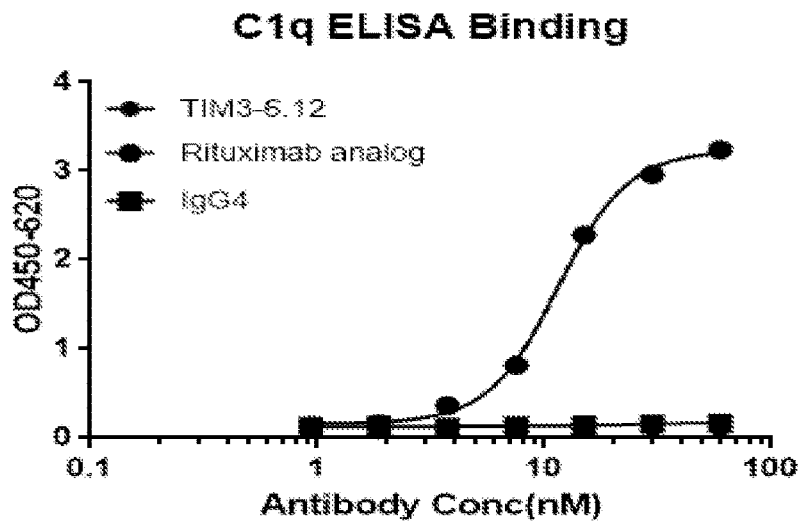
FIG. 7 shows that anti-TIM-3 antibodies of the invention do not bind to C1q.

As shown in FIG. 7, antibody TIM3-6.12 did not bind to C1q.

Example 13 Anti-TIM-3 Antibodies Did not Induce Antibody-Dependent Cell-Mediated Cytotoxicity (ADCC)

Antibody-Dependent Cell-Mediated Cytotoxicity (ADCC) assay on CHO-K1-TIM-3 cells were performed. CHO-K1-TIM-3 cells as generated in Example 8 were seeded at a density of 10,000 cells per well and were pre-incubated with 100 nM or 10 nM anti-TIM-3 antibodies in assay buffer (Phenol red free MEM medium+1% FBS) for 30 min. PBMC effector cells from healthy donors were added to initiate the ADCC effects at E/T ratios at 10:1, 25:1 or 50:1. The ADCC effect of the Rituximab analog on Raji (CBTCCCAS, cat #TCHu 44) was used as an internal control to assure the assay quality. After incubation in a 37° C., 5% $CO_2$ incubator for 24 hours, cell supernatants were then collected for measuring released LDH using a cytotoxicity LDH assay kit (Dojindo, Cat #CK12). Absorbance at $OD_{490nm}$ was read on F50 (Tecan). The percentages of cell lysis were calculated according the formula below, % Cell lysis=$100 \times (OD_{sample} - OD_{target\ cells\ plus\ effector\ cells})/(OD_{Maximum\ release} - OD_{Minimum\ release})$ Data was analyzed by Graphpad Prism.

Figure 8:
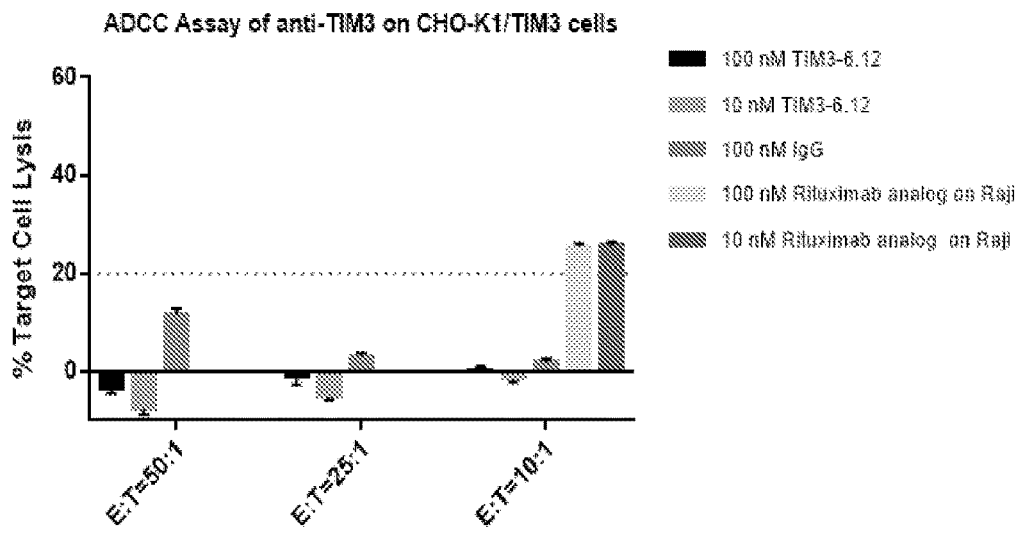
FIG. 8 shows that anti-TIM-3 antibodies of the invention do not induce ADCC on CHO-K1-TIM-3 cells.
Figure 9:
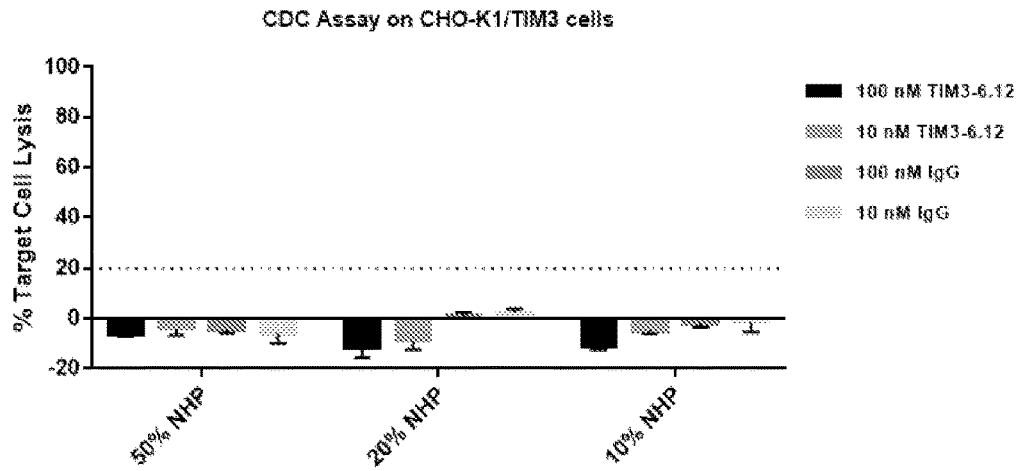
FIG. 9 shows that anti-TIM-3 antibodies of the invention do not induce CDC on CHO-K1-TIM-3 cells.

As shown in FIG. 8, anti-TIM-3 antibody TIM3-6.12 had no ADCC activity on CHO-K1-Tim3 cells.

Example 14 Anti-TIM-3 Antibodies Did not Induce Complement-Dependent Cytotoxicity (CDC)

Complement-Dependent Cytotoxicity (CDC) assay on CHO-K1-TIM-3 cells were performed. CHO-K1-TIM-3 cells as generated in Example 8 were seeded at a density of 5,000 cells per well and were pre-incubated with 100 nM or 10 nM antibodies in assay buffer (Phenol red free MEM medium+1% FBS) for 30 min. The plates were then added with plasma from healthy donors at the concentration of 10 vol %, 20 vol % and 50 vol % to initiate the CDC effects. After incubation in a 37° C., 5% $CO_2$ incubator for 4 hours, cells were added with Cell-Titer Glo reagent (Promega, Cat #G7572) and the RLU data was read on F200 (Tecan). The percentages of cell lysis were calculated according the formula below, % Cell lysis=$100 \times (1-(RLU_{sample}/(RLU_{cell+NHP}))$ in which NHP represented normal human plasma.

Data analyzed by Graphpad Prism showed that anti-TIM-3 antibody TIM3-6.12 had no CDC activity on CHO-K1-TIM-3 cells.

Example 15 Pharmacokinetic of Anti-TIM-3 Antibodies in Rat

Pharmacokinetic profile of TIM3-6.12 in rat was evaluated. In the study, TIM3-6.12 was injected intravenously into rats at a dose of 10 mg/kg. Blood samples were obtained at various time points between 0 and 360 hours (0-15 days). All samples were processed to plasma, stored frozen at −70-86° C. until analyzed. The concentration of TIM3-6.12 present in the serum was determined by ELISA.

Table 3 showed the pharmacokinetic properties as determined above.

TABLE 3

Summary of pharmacokinetic properties of TIM3-6.12

| Dose | | $T_{1/2}$ (h) | $AUC_{last}$ (h * μg/mL) | $AUC_{INF\_obs}$ (h * μg/mL) | $V_{Z\_obs}$ (mL/kg) | $Cl_{obs}$ (mL/h/kg) |
|---|---|---|---|---|---|---|
| 10 mg/kg | N | 3 | 3 | 3 | 3 | 3 |
| | Mean | 329.84 | 24219.28 | 46140.43 | 101.24 | 0.25 |
| | SD | 152.13 | 2946.33 | 18736.73 | 16.14 | 0.13 |

$AUC_{last}$(Area under the plasma level curve from t = 0 to last measurable plasma drug concentration at time t),
$AUC_{INF\_obs}$(Area under concentration-time curve 0-∞,
$V_{z\_obs}$(The volume of distribution,
$Cl_{obs}$Clearance).

AUC$_{last}$ (Area under the plasma level time curve from t=0 to last measurable plasma drug concentration at time t), AUC$_{INF\_obs}$ (Area under concentration-time curve 0-∞), V$_{z\_obs}$ (The volume of distribution), Cl$_{obs}$ (Clearance).

Sequences in the present application are summarized below.

---

Description/Sequence/SEQ ID NO.

---

VH-CDR1 for TIM3-6
SYTIS (SEQ ID NO: 1)

VH-CDR1 for TIM3-6.10, TIM3-6.11 and TIM3-6.12
SYTIY (SEQ ID NO: 2)

VH-CDR1 for TIM3-4G7
SYAMS (SEQ ID NO: 3)

VH-CDR1 for TIM3-11
SNSAAWN (SEQ ID NO: 4)

VH-CDR 2 for TIM3-6
RIIPILGTANYAQKFQG (SEQ ID NO: 5)

VH-CDR2 for TIM3-6.10, TIM3-6.11 and TIM3-6.12
SIIPILGTANYAQKFQG (SEQ ID NO: 6)

VH-CDR2 for TIM3-4G7
GISGSGGSTYYADSVKG (SEQ ID NO: 7)

VH-CDR2 for TIM3-11
RTYYRSKWYNDYAVSVKS (SEQ ID NO: 8)

VH-CDR 3 for TIM3-6, TIM3-6.10, TIM3-6.11 and TIM3-6.12
ASHTI (SEQ ID NO: 9)

VH-CDR3 for TIM3-4G7
SYYDDAFDI (SEQ ID NO: 10)

VH-CDR3 for TIM3-11
DQAAGFPQPYIYGMDV (SEQ ID NO: 11)

VL-CDR1 for TIM3-6
ASSTGAVTSGYSPN (SEQ ID NO: 12)

VL-CDR1 for TIM3-6.10
ASSTGAVTSGNTPN (SEQ ID NO: 13)

VL-CDR1 for TIM3-6.11 and TIM3-6.12
ASSTGAVTSGYTPN (SEQ ID NO: 14)

VL-CDR1 for TIM3-4G7
RASQSVTKDLVA (SEQ ID NO: 15)

VL-CDR1 for TIM3-11
TGNSNNVGNQGAA (SEQ ID NO: 16)

VL-CDR 2 for TIM3-6, TIM3-6.10, TIM3-6.11
TTSNRHS (SEQ ID NO: 17)

VL-CDR2 for TIM3-6.12
TTNNRHS (SEQ ID NO: 18)

VL-CDR2 for TIM3-4G7
GASSRAT (SEQ ID NO: 19)

VL-CDR2 for TIM3-11
RTNNRPS (SEQ ID NO: 20)

VL-CDR 3 for TIM3-6, TIM3-6.10, TIM3-6.11 and TIM3-6.12
LLYYGGAWV (SEQ ID NO: 21)

VL-CDR3 for TIM3-4G7
QQYGRSPLT (SEQ ID NO: 22)

VL-CDR3 for TIM3-11
SGWDSSLNEGV (SEQ ID NO: 23)

VH for TIM3-6

| Description/<br>Sequence/SEQ ID NO. |
|---|

QVQLVQSGAEVKKPGSSVKVSCKASGGTFSSYTISWVRQAPGQGLEWMGRIIPILGTANYAQKFQGR
VTITADESTSTAYMELSSLRSEDTAVYYCASASHTIWGKGTLVTVSS (SEQ ID NO: 24)

CAGGTGCAGCTGGTGCAGTCTGGCGCCGAGGTGAAGAAGCCAGGCTCCAGCGTGAAGGTGTCCT
GCAAGGCCTCCGGCGGCACCTTCTCTTCCTACACAATCTCCTGGGTGAGGCAGGCTCCAGGACAG
GGACTGGAGTGGATGGGCCGGATCATCCCTATCCTGGGCACCGCCAACTACGCTCAGAAGTTTCA
GGGCAGAGTGACCATCACAGCCGACGAGTCTACCTCCACAGCTTATATGGAGCTGAGCTCTCTGC
GCTCCGAGGATACCGCCGTGTACTATTGTGCCTCCGCCTCCCACACAATCTGGGGCAAGGGCACC
CTGGTGACAGTGTCCAGC (SEQ ID NO: 37)

VH for TIM3-6.10, TIM3-6.11 and TIM3-6.12
QVQLVQSGAEVKKPGSSVKVSCKASGGTFSSYTIYWVRQAPGQGLEWMGSIIPILGTANYAQKFQGR
VTITADESTSTAYMELSSLRSEDTAVYYCASASHTIWGQGTLVTVSS (SEQ ID NO: 25)

CAGGTGCAGCTGGTGCAGTCCGGCGCTGAGGTGAAGAAGCCCGGCAGCTCCGTGAAGGTGTCCT
GCAAGGCCTCCGGCGGCACCTTCTCCTCCTACACCATCTACTGGGTGAGGCAAGCCCCTGGCCAG
GGACTGGAGTGGATGGGCTCCATCATCCCTATCCTGGGCACCGCCAACTACGCCCAGAAGTTCCA
GGGAAAGGGTGACCATCACCGCCGACGAGAGCACCTCCACCGCCTACATGGAGCTGTCCTCCCTGC
GGTCCGAGGACACCGCTGTGTACTACTGCGCCAGCGCTTCCCACACCATCTGGGGCCAGGGCACC
CTGGTGACCGTGTCCAGC (SEQ ID NO: 38)

VH for TIM3-4G7
EVQLVETGGGLVQPGGSLRLSCAASGFTFSSYAMSWVRQAPGKGLEWVSGISGSGGSTYYADSVKG
RFTTSRDNSENTLYLQMNSLRAEDTAVYYCAGSYYDDAFDIWGQGTLVTVSS (SEQ ID NO: 26)

GAGGTGCAGCTGGTGGAGACCGGAGGAGGACTGGTGCAGCCAGGAGGATCCCTGAGACTGAGCT
GCGCCGCTTCTGGCTTCACATTTTCCAGCTACGCTATGAGCTGGGTGCGCCAGGCTCCTGGCAAG
GGACTGGAGTGGGTGTCTGGCATCAGCGGCTCTGGCGGCTCTACCTACTATGCCGACTCCGTGAA
GGGCAGGTTCACCACATCCCGGGATAACAGCGAGAATACCCTGTATCTGCAGATGAACTCCCTGA
GGGCCGAGGACACAGCCGTGTACTATTGTGCCGGCTCCTACTATGACGATGCTTTTGATATCTGG
GGCCAGGGCACCCTGGTGACAGTGTCTTCC (SEQ ID NO: 39)

VH for TIM3-11
QVQLQQSGPGLVKPSQTLSLTCAISGDSVSSNSAAWNWIRQSPSRGLEWLGRTYYRSKWYNDYAVS
VKSRITINPDTSKNQFSLQLNSVTPEDTAVYYCARDQAAGFPQPYIYGMDVWGKGTMVTVSS
(SEQ ID NO: 27)

CAGGTGCAGCTGCAGCAGAGCGGCCCTGGACTGGTGAAGCCTTCCCAGACCCTGTCCCTGACCTG
CGCCATCTCCGGCGATTCCGTGTCCTCCAACAGCGCCGCCTGGAACTGGATCAGGCAGAGCCCTA
GCAGGGGCCTGGAGTGGCTGGGAAGGACCTACTACCGGTCCAAGTGGTACAACGACTACGCCGT
GTCCGTGAAGTCCAGGATCACCATCAACCCCGACACCTCCAAGAACCAGTTCTCCCTGCAGCTGA
ACTCCGTGACCCCCGAGGACACCGCCGTGTACTACTGTGCCCGGGATCAGGCTGCCGGCTTTCCT
CAGCCTTACATCTACGGCATGGACGTGTGGGGCAAGGGCACCATGGTGACCGTGTCCTCC
(SEQ ID NO: 40)

VL for TIM3-6
QAVVTQEPSLTVSPGGTVTLTCASSTGAVTSGYSPNWFQQRPGQAPRALIYTTSNRHSWTPARFSGSL
LGGKAALTLSGVQPEDEADYYCLLYYGGAWVFGGGTKLTVLG (SEQ ID NO: 28)

CAGGCCGTGGTGACCCAGGAGCCTTCCCTGACCGTGTCCCCTGGAGGCACCGTGACCCTGACCTG
TGCTTCCTCCACAGGCGCTGTGACCTCCGGCTACTCCCCCAACTGGTTCCAGCAGAGGCCTGGCC
AGGCTCCTAGGGCTCTGATCTACACCACCTCCAACAGGCACTCCTGGACCCCTGCCAGGTTCTCC
GGAAGCCTGCTGGGCGGAAAGGCTGCTCTGACACTGTCCGGCGTGCAGCCTGAAGACGAGGCCG
ACTACTACTGCCTGCTGTACTACGGCGGCGCCTGGGTGTTCGGCGGCGGCACCAAGCTGACAGTG
CTGGGA (SEQ ID NO: 41)

VL for TIM3-6.10
QAVVTQEPSLTVSPGGTVTLTCASSTGAVTSGX1TPNWFQQRPGQAPRALIYTTX2NRHSWTPARFSGS
LLGGKAALTLSGVQPEDEADYYCLLYYGGAWVFGGGTKLTVLG X$_1$ = N, X$_2$ = S (SEQ ID NO: 29)

CAGGCCGTGGTGACCCAGGAGCCAAGCCTGACAGTGTCTCCAGGAGGAACCGTGACACTGACCT
GCGCCTCCAGCACAGGCGCTGTGACCTCTGGCAACACACCCAATTGGTTCCAGCAGAGGCCAGG
ACAGGCTCCTCGGGCTCTGATCTACACCACATCCAACAGACACAGCTGGACCCCTGCTCGCTTTT
CTGGATCCCTGCTGGGAGGCAAGGCCGCTCTGACACTGTCCGGAGTGCAGCCAGAGGACGAGGC
TGATTACTATTGTCTGCTGTACTATGGAGGAGCTTGGGTGTTCGGAGGAGGAACAAAGCTGACCG
TGCTGGGC (SEQ ID NO: 42)

VL for TIM3-6.11
QAVVTQEPSLTVSPGGTVTLTCASSTGAVTSGX1TPNWFQQRPGQAPRALIYTTX2NRHSWTPARFSGS
LLGGKAALTLSGVQPEDEADYYCLLYYGGAWVFGGGTKLTVLG X$_1$ = Y, X$_2$ = S (SEQ ID NO: 29)

CAGGCCGTGGTGACCCAGGAGCCAAGCCTGACAGTGTCTCCAGGAGGAACCGTGACACTGACCT
GCGCCTCCAGCACAGGCGCTGTGACCTCTGGCTACACACCCAACTGGTTCCAGCAGAGGCCAGG
ACAGGCTCCTCGGGCTCTGATCTATACCACATCCAATAGACACAGCTGGACCCCTGCTCGCTTTC
TGGATCCCTGCTGGGAGGCAAGGCCGCTCTGACACTGTCCGGAGTGCAGCCAGAGGACGAGGCT
GATTACTATTGTCTGCTGTACTATGGAGGAGCTTGGGTGTTCGGAGGAGGAACAAAGCTGACCGT

| Description/Sequence/SEQ ID NO. |
| --- |
| GCTGGGC (SEQ ID NO: 43) |
| |
| VL for TIM3-6.12<br>QAVVTQEPSLTVSPGGTVTLTCASSTGAVTSGX₁TPNWFQQRPGQAPRALIYTTX₂NRHSWTPARFSGS<br>LLGGKAALTLSGVQPEDEADYYCLLYYGGAWVFGGGTKLTVLG  X₁ = Y, X₂ = N<br>(SEQ ID NO: 29) |
| |
| CAGGCCGTGGTGACCCAGGAGCCAAGCCTGACAGTGTCTCCAGGAGGAACCGTGACACTGACCT<br>GCGCCTCCAGCACAGGCGCTGTGACCTCTGGCTACACACCCAACTGGTTCCAGCAGAGGCCAGG<br>ACAGGCTCCTCGGGCTCTGATCTATACCACAAACAATAGACACTCCTGGACCCCTGCTCTTTTC<br>TGGATCCCTGCTGGGAGGCAAGGCCGCTCTGACACTGAGCGGAGTGCAGCCAGAGGACGAGGCT<br>GATTACTATTGTCTGCTGTACTATGGAGGAGCTTGGGTGTTCGGAGGAGGAACAAAGCTGACCGT<br>GCTGGGC (SEQ ID NO: 44) |
| |
| VL for TIM3-4G7<br>ETTLTQSPATLSLSPGDTATLSCRASQSVTKDLVAWYQQRPGQAPRLLLYGASSRATGIPDRFSGSGS<br>GTDFTLTISRLEPEDFAVYYCQQYGRSPLTFGGGTKVEIK (SEQ ID NO: 30) |
| |
| GAGACCACCCTGACCCAGTCCCCCGCTACACTGTCCCTGTCCCCTGGCGACACCGCCACACTGTC<br>CTGCAGGGCCTCCCAGAGCGTGACCAAGGACCTGGTGGCCTGGTACCAGCAGAGGCCTGGACAG<br>GCCCCTAGGCTGCTGCTGTACGGCGCTTCCTCCAGGGCCACAGGCATCCCTGATAGGTTCTCCGG<br>CAGCGGCTCCGGCACCGATTTCACCCTGACCATCTCCAGGCTGGAGCCCGAGGACTTCGCCGTGT<br>ACTACTGCCAGCAGTACGGCAGGTCCCCCCTGACCTTTGGAGGCGGCACCAAGGTGGAGATCAA<br>G (SEQ ID NO: 45) |
| |
| VL for TIM3-11<br>LPVLTQPPSVSKGLRQTATLTCTGNSNNVGNQGAAWLQQHQGHPPKLLTYRTNNRPSGISERFSASRS<br>GNTASLTITGLQPEDEADYYCSGWDSSLNEGVFGGGTKLTVLG (SEQ ID NO: 31) |
| |
| CTGCCCGTGCTGACCCAGCCTCCTTCCGTGAGCAAGGGCCTGAGGCAGACAGCCACCCTGACCTG<br>CACCGGCAACTCCAACAACGTGGGCAACCAGGGCGCTGCTTGGCTGCAGCAGCACCAGGGCCAC<br>CCTCCTAAGCTGCTGACCTACAGGACCAACAACAGGCCCTCCGGCATCTCCGAGAGGTTCTCCGC<br>CTCTAGGTCCGGCAACACCGCCTCCCTGACCATCACCGGACTGCAGCCCGAGGACGAGGCCGACT<br>ACTACTGCTCCGGCTGGGACAGCTCCCTGAACGAGGGCGTGTTCGGCGGCGGCACCAAGCTGAC<br>AGTGCTGGGA (SEQ ID NO: 46) |
| |
| CH for TIM3-6, TIM3-4G7 and TIM3-11<br>ASTKGPSVFPLAPCSRSTSESTAALGCLVKDYFPEPVTVSWNSGALTSGVHTFPAVLQSSGLYSLSSVV<br>TVPSSSLGTKTYTCNVDHKPSNTKVDKRVESKYGPPCPPCPAPEFLGGPSVFLFPPKPKDTLMISRTPE<br>VTCVVVDVSQEDPEVQFNWYVDGVEVHNAKTKPREEQFNSTYRVVSVLTVLHQDWLNGKEYKCKV<br>SNKGLPSSIEKTISKAKGQPREPQVYTLPPSQEEMTKNQVSLTCLVKGFYPSDIAVEWESNGQPENNY<br>KTTPPVLDSDGSFFLYSRLTVDKSRWQEGNVFSCSVMHEALHNHYTQKSLSLSLGK (SEQ ID NO: 32) |
| |
| GCTAGCACAAAGGGACCTTCCGTGTTCCCACTGGCCCCCTGCTCCAGAAGCACATCTGAGTCCAC<br>CGCCGCTCTGGGCTGTCTGGTGAAGGACTACTTCCCTGAGCCAGTGACCGTGTCCTGGAACAGCG<br>GCGCCCTGACATCCGGAGTGCACACCTTTCCCGCCGTGCTCCAGTCCAGCGGACTGTACAGCCTG<br>TCTTCCGTGGTGACAGTGCCCAGCTCTTCCCTGGGCACCAAGACATATACCTGCAACGTGGACCA<br>TAAGCCTAGCAATACCAAGGTGGATAAGAGGGTGGAGTCTAAGTACGGACCACCTTGCCCACCA<br>TGTCCAGCTCCTGAGTTTCTGGGAGGACCATCCGTGTTCCTGTTTCCTCCAAAGCCTAAGGACACC<br>CTGATGATCTCTCGGACACCTGAGGTGACCTGCGTGGTGGTGGACGTGTCCCAGGAGGACCCCGA<br>GGTGCAGTTCAACTGGTACGTGGATGGCGTGGAGGTGCACAATGCTAAGACCAAGCCAAGAGAG<br>GAGCAGTTTAATAGCACATACCGCGTGGTGTCTGTGCTGACCGTGCTGCATCAGGATTGGCTGAA<br>CGGCAAGGAGTATAAGTGCAAGGTGAGCAATAAGGGCCTGCCCAGCTCTATCGAGAAGACAATC<br>TCTAAGGCTAAGGGACAGCCTCGCGAGCCACAGGTGTACACCCTGCCCCCTTCCCAGGAGGAGA<br>TGACAAAGAACCAGGTGAGCCTGACCTGTCTGGTGAAGGGCTTCTATCCATCTGACATCGCTGTG<br>GAGTGGGAGTCCAACGGCCAGCCCGAGAACAATTACAAGACCACACCACCCGTGCTGGACTCTG<br>ATGGCTCCTTCTTTCTGTATTCCAGGCTGACAGTGGATAAGAGCCGGTGGCAGGAGGGCAACGTG<br>TTTAGCTGCTCTGTGATGCACGAGGCTCTGCACAATCATTATACCCAGAAGTCCCTGAGCCTGTCT<br>CTGGGCAAG (SEQ ID NO: 47) |
| |
| CH for TIM3-6.10, TIM3-6.11 and TIM3-6.12<br>ASTKGPSVFPLAPSSKSTSGGTAALGCLVKDYFPEPVTVSWNSGALTSGVHTFPAVLQSSGLYSLSSV<br>VTVPSSSLGTQTYICNVNHKPSNTKVDKKVEPKSCDKTHTCPPCPAPEAAGGPSVFLFPPKPKDTLMIS<br>RTPEVTCVVVAVSHEDPEVKFNWYVDGVEVHNAKTKPREEQYNSTYRVVSVLTVLHQDWLNGKEY<br>KCKVSNKALAAPIEKTISKAKGQPREPQVYTLPPSRDELTKNQVSLTCLVKGFYPSDIAVEWESNGQP<br>ENNYKTTPPVLDSDGSFFLYSKLTVDKSRWQQGNVFSCSVMHEALHNHYTQKSLSLSPGK<br>(SEQ ID NO: 33) |
| |
| GCTAGCACCAAGGGACCATCCGTGTTCCCACTGGCCCCCTCCAGCAAGTCCACCAGCGGAGGAA<br>CAGCCGCTCTGGGATGCCTGGTGAAGGACTACTTCCCAGAGCCCGTGACAGTGAGCTGGAACTCT<br>GGCGCCCTGACCAGCGGAGTGCACACATTTCCCGCCGTGCTCCAGTCTTCCGGCCTGTACTCTCTG<br>AGCTCTGTGGTGACCGTGCCCTCCAGCTCTCTGGGCACCCAGACATATATCTGCAACGTGAATCA<br>CAAGCCAAGCAATACAAAGGTGGACAAGAAGGTGGAGCCCAAGTCTTGTGATAAGACCCATACA<br>TGCCCCCCTTGTCCTGCTCCAGAGGCTGCTGGAGGACCAAGCGTGTTCCTGTTTCCACCCAAGCCT<br>AAGGACACCCTGATGATCTCCAGGACCCCCGAGGTGACATGCGTGGTGGTGGCTGTGAGCCACG<br>AGGACCCCGAGGTGAAGTTTAACTGGTACGTGGATGGCGTGGAGGTGCATAATGCTAAGACCAA<br>GCCTAGGGAGGAGCAGTACAACTCTACCTATCGGGTGGTGTCCGTGCTGACAGTGCTGCACCAGG |

| Description/<br>Sequence/SEQ ID NO. |
|---|
| ACTGGCTGAACGGCAAGGAGTATAAGTGCAAGGTGTCTAATAAGGCCCTGGCTGCTCCTATCGA<br>GAAGACCATCTCCAAGGCCAAGGGCCAGCCTAGAGAGCCACAGGTGTACACACTGCCTCCATCT<br>CGCGACGAGCTGACCAAGAACCAGGTGTCCCTGACATGTCTGGTGAAGGGCTTCTATCCTTCCGA<br>CATCGCTGTGGAGTGGGAGAGCAACGGCCAGCCAGAGAACAATTACAAGACCACACCCCCTGTG<br>CTGGACTCCGATGGCAGCTTCTTTCTGTATAGCAAGCTGACCGTGGATAAGTCCAGGTGGCAGCA<br>GGGCAACGTGTTTTCTTGCTCCGTGATGCATGAGGCTCTGCACAATCATTATACACAGAAGAGCC<br>TGTCTCTGTCCCCTGGCAAGTGA (SEQ ID NO: 48)<br><br>CL for TIM3-6 and TIM3-11<br>QPKAAPSVTLFPPSSEELQANKATLVCLISDFYPGAVTVAWKADSSPVKAGVETTTPSKQSNNKYAAS<br>SYLSLTPEQWKSHRSYSCQVTHEGSTVEKTVAPTECS (SEQ ID NO: 34)<br><br>CAGCCCAAGGCTGCCCCTTCCGTGACCCTGTTTCCCCCCTCCTCCGAGGAGCTGCAGGCCAACAA<br>GGCCACCCTGGTGTGCCTGATCTCCGACTTCTACCCTGGCGCTGTGACCGTGGCTTGGAAGGCCG<br>ATTCCTCCCCTGTGAAGGCCGGCGTGGAGACCACAACCCCCTCCAAGCAGTCCAACAACAAGTAC<br>GCCGCTTCCTCCTACCTGTCCCTGACCCCCGAGCAGTGGAAGTCCCACAGGTCCTACTCCTGCCA<br>GGTGACCCACGAGGGCTCCACCGTGGAGAAGACAGTGGCCCCCACCGAGTGCTCCTGA<br>(SEQ ID NO: 49)<br><br>CL for TIM3-6.10, TIM3-6.11 and TIM3-6.12<br>QPKAAPSVTLFPPSSEELQANKATLVCLISDFYPGAVTVAWKADSSPVKAGVETTTPSKQSNNKYAAS<br>SYLSLTPEQWKSHRSYSCQVTHEGSTVEKTVAPTEC (SEQ ID NO: 35)<br><br>CL for TIM3-4G7<br>RTVAAPSVFIFPPSDEQLKSGTASVVCLLNNFYPREAKVQWKVDNALQSGNSQESVTEQDSKDSTYSL<br><br>SSTLTLSKADYEKHKVYACEVTHQGLSSPVTKSFNRGEC (SEQ ID NO: 36)<br>CGTACGGTGGCCGCTCCATCCGTGTTCATCTTTCCCCCTAGCGACGAGCAGCTGAAGAGCGGCAC<br>CGCCTCTGTGGTGTGCCTGCTGAACAATTTCTACCCCAGGGAGGCCAAGGTGCAGTGGAAGGTGG<br>ATAACGCTCTCCAGAGCGGCAATTCTCAGGAGTCCGTGACCGAGCAGGACAGCAAGGATTCTAC<br>ATATTCCCTGTCCAGCACCCTGACACTGTCTAAGGCCGACTACGAGAAGCACAAGGTGTATGCTT<br>GCGAGGTGACACATCAGGGCCTGTCTTCCCCCGTGACAAAGTCCTTTAACCGGGGCGAGTGTTGA<br>(SEQ ID NO: 50)<br><br>Linker peptide<br>GGGGSGGGGSGGGGS (SEQ ID NO: 51)<br><br>Human IgG control<br>QVQLQESGGGVVRPGGSLRLSCAASGFTFDDYGMSWVRQAPGKGLEWVSGINWSGGSTYYADSVK<br>GRSTISRDNSKNTLYLQMNSLRAEDTAVYYCATGGYWGQGTLVTVSSASTKGPSVFPLAPCSRSTSES<br>TAALGCLVKDYFPEPVTVSWNSGALTSGVHTFPAVLQSSGLYSLSSVVTVPSSSLGTKTYTCNVDHKP<br>SNTKVDKRVESKYGPPCPPCPAPEFLGGPSVFLFPPKPKDTLMISRTPEVTCVVVDVSQEDPEVQFNW<br>YVDGVEVHNAKTKPREEQFNSTYRVVSVLTVLHQDWLNGKEYKCKVSNKGLPSSIEKTISKAKGQPR<br>EPQVYTLPPSQEEMTKNQVSLTCLVKGFYPSDIAVEWESNGQPENNYKTTPPVLDSDGSFFLYSRLTV<br>DKSRWQEGNVFSCSVMHEALHNHYTQKSLSLSLGK<br>DIRLTQSPSSLSASVGDRVTITCRASQSISSYLNWYQQKPGKAPKLLIYAASSLQGGVPSRFSGSGSGTD<br>FTLTISSLQPEDSATYYCQQSYSTPYTFGQGTKLTVLGRTVAAPSVFIFPPSDEQLKSGTASVVCLLNNF<br>YPREAKVQWKVDNALQSGNSQESVTEQDSKDSTYSLSSTLTLSKADYEKHKVYACEVTHQGLSSPVT<br>KSFNRGEC (SEQ ID NO: 52)<br><br>Heavy chain of ABTIM3 analog<br>QVQLVQSGAEVKKPGASVKVSCKASGYTFTSYNMHWVRQAPGQGLEWIGDIYPGSGDTSYNQKFK<br>GRATMTADKSTSTVYMELSSLRSEDTAVYYCARVGGAFPMDYWGQGTLVTVSSASTKGPSVFPLAP<br>CSRSTSESTAALGCLVKDYFPEPVTVSWNSGALTSGVHTFPAVLQSSGLYSLSSVVTVPSSSLGTKTYT<br>CNVDHKPSNTKVDKRVESKYGPPCPPCPAPEFLGGPSVFLFPPKPKDTLMISRTPEVTCVVVDVSQEDP<br>EVQFNWYVDGVEVHNAKTKPREEQFNSTYRVVSVLTVLHQDWLNGKEYKCKVSNKGLPSSIEKTIS<br>KAKGQPREPQVYTLPPSQEEMTKNQVSLTCLVKGFYPSDIAVEWESNGQPENNYKTTPPVLDSDGSFF<br>LYSRLTVDKSRWQEGNVFSCSVMHEALHNHYTQKSLSLSLG (SEQ ID NO: 53)<br><br>Light chain of ABTIM3 analog<br>DIVLTQSPDSLAVSLGERATINCRASESVEYYGTSLMQWYQQKPGQPPKLLIYAASNVESGVPDRFSG<br>SGSGTDFTLTISSLQAEDVAVYYCQQSRKDPSTFGGGTKVEIKRTVAAPSVFIFPPSDEQLKSGTASVV<br>CLLNNFYPREAKVQWKVDNALQSGNSQESVTEQDSKDSTYSLSSTLTLSKADYEKHKVYACEVTHQ<br>GLSSPVTKSFNRGEC (SEQ ID NO: 54)<br><br>TIM3-mFc protein<br>SEVEYRAEVGQNAYLPCFYTPAAPGNLVPVCWGKGACPVFECGNVVLRTDERDVNYWTSRYWLNG<br>DFRKGDVSLTIENVTLADSGIYCCRIQIPGIMNDEKFNLKLVIKPAKVTPAPTRQRDFTAAFPRMLTTR<br>GHGPAETQTLGSLPDINLTQISTLANVPRDCGCKPCICTVPEVSSVFIFPPKPKDVLTITLTPKVTCVVV<br>DISKDDPEVQFSWFVDDVEHTAQTQPREEQFNSTFRSVSELPIMHQDWLNGKEFKCRVNSAAFPAPI<br>EKTISKTKGRPKAPQVYTIPPPKEQMAKDKVSLTCMITDFFPEDITVEWQWNGQPAENYKNTQPIMDT<br>DGSYFVYSKLNVQKSNWEAGNTFTCSVLHEGLHNHHTEKSLSHSPGK (SEQ ID NO: 55)<br><br>heavy chain of Rituximab<br>QVQLQQPGAELVKPGASVKMSCKASGYTFTSYNMHWVKQTPGRGLEWIGAIYPGNGDTSYNQKFK<br>GKATLTADKSSSTAYMQLSSLTSEDSAVYYCARSTYYGGDWYFNVWGAGTTVTVSAASTKGPSVFP |

| Description/Sequence/SEQ ID NO. |
|---|
| LAPSSKSTSGGTAALGCLVKDYFPEPVTVSWNSGALTSGVHTFPAVLQSSGLYSLSSVVTVPSSSLGTQ<br>TYICNVNHKPSNTKVDKKVEPKSCDKTHTCPPCPAPELLGGPSVFLFPPKPKDTLMISRTPEVTCVVVD<br>VSHEDPEVKFNWYVDGVEVHNAKTKPREEQYNSTYRVVSVLTVLHQDWLNGKEYKCKVSNKALPA<br>PIEKTISKAKGQPREPQVYTLPPSRDELTKNQVSLTCLVKGFYPSDIAVEWESNGQPENNYKTTPPVLD<br>SDGSFFLYSKLTVDKSRWQQGNVFSCSVMHEALHNHYTQKSLSLSPGK (SEQ ID NO: 56)<br><br>light chain of Rituximab<br>QIVLSQSPAILSASPGEKVTMTCRASSSVSYIHWFQQKPGSSPKPWIYATSNLASGVPVRFSGSGSGTSY<br>SLTISRVEAEDAATYYCQQWTSNPPTFGGGTKLEIKRTVAAPSVFIFPPSDEQLKSGTASVVCLLNNFY<br>PREAKVQWKVDNALQSGNSQESVTEQDSKDSTYSLSSTLTLSKADYEKHKVYACEVTHQGLSSPVTK<br>SFNRGEC (SEQ ID NO: 57)<br><br>SEQ ID NOs:1-36 and 51-57: amino acid sequence; SEQ ID NOs:37-50:<br>nucleotide sequence |

We claim:

1. An isolated antibody, or an antigen-binding portion thereof, comprising a heavy chain variable region comprising a V$_H$CDR1 region, a V$_H$CDR2 region and a V$_H$CDR3 region, wherein the V$_H$CDR1 region, the V$_H$CDR2 region and the V$_H$CDR3 region comprise or consist of amino acid sequences of
   (1) SEQ ID NOs: 2, 6 and 9, respectively; or
   (2) SEQ ID NOs: 1, 5 and 9, respectively;
   comprising a light chain variable region comprising a V$_L$CDR1 region, a V$_L$CDR2 region and a V$_L$CDR3 region, wherein the V$_L$CDR1 region, the V$_L$CDR2 region and the V$_L$CDR3 region comprise or consist of amino acid sequences of
   (1) SEQ ID NOs: 14, 18 and 21, respectively;
   (2) SEQ ID NOs: 12, 17 and 21, respectively;
   (3) SEQ ID NOs: 13, 17 and 21, respectively; or
   (4) SEQ ID NOs: 14, 17 and 21, respectively;
   wherein the antibody or antigen-binding fragment thereof binds human TIM-3.

2. The isolated antibody or the antigen-binding portion thereof according to claim 1, wherein the V$_H$ CDR1 region, the V$_H$ CDR2 region, the V$_H$ CDR3 region, the V$_L$CDR1 region, the V$_L$CDR2 region and the V$_L$CDR3 region comprise or consist of amino acid sequences of
   (1) SEQ ID NO: 1, 5, 9, 12, 17 and 21, respectively;
   (2) SEQ ID NO: 2, 6, 9, 13, 17 and 21, respectively;
   (3) SEQ ID NO: 2, 6, 9, 14, 17 and 21, respectively; or
   (4) SEQ ID NO: 2, 6, 9, 14, 18 and 21, respectively.

3. The isolated antibody or the antigen-binding portion thereof of claim 2, comprising a heavy chain variable region comprising an amino acid sequence having at least 90% identity to SEQ ID NOs: 25 or 24, and/or comprising a light chain variable region comprising an amino acid sequence having at least 90% identity to SEQ ID NOs: 29 or 28, wherein $X_1=Y$ and $X_2=N$; or $X_1=N$ and $X_2=S$; or $X_1=Y$ and $X_2=S$ in SEQ ID NO:29.

4. The isolated antibody or the antigen-binding portion thereof of claim 2, comprising a heavy chain variable region and a light chain variable region, wherein the heavy chain and the light chain variable regions comprise amino acid sequences having at least 90% identity to (1) SEQ ID NOs: 25 and 29, respectively, wherein $X_1=Y$ and $X_2=N$; or $X_1=N$ and $X_2=S$; or $X_1=Y$ and $X_2=S$ in SEQ ID NO:29; or (2) SEQ ID NOs: 24 and 28, respectively.

5. The isolated antibody or the antigen-binding portion thereof of claim 2, comprising a heavy chain constant region comprising an amino acid sequence having at least 90% identity to SEQ ID NOs: 33 or 32, and/or a light chain constant region comprising an amino acid sequence having at least 90% identity to SEQ ID NOs: 35, 34 or 36.

6. The isolated antibody or the antigen-binding portion thereof of claim 2, comprising a heavy chain variable region and a light chain variable region, wherein the heavy chain and the light chain variable regions comprise or consist of amino acid sequences represented by (1) SEQ ID NOs: 25 and 29, respectively, wherein $X_1=Y$ and $X_2=N$; or $X_1=N$ and $X_2=S$; or $X_1=Y$ and $X_2=S$ in SEQ ID NO:29; or (2) SEQ ID NOs: 24 and 28, respectively.

7. The isolated antibody or the antigen-binding portion thereof of claim 2, comprising
 (a) a heavy chain variable region comprising an amino acid sequence represented by SEQ ID NO: 25, a light chain variable region comprising an amino acid sequence represented by SEQ ID NO:29, a heavy chain constant region comprising an amino acid sequence represented by SEQ ID NO:33 and a light chain constant region comprising an amino acid sequence represented by SEQ ID NO:35, wherein $X_1=Y$ and $X_2=N$; or $X_1=N$ and $X_2=S$; or $X_1=Y$ and $X_2=S$ in SEQ ID NO:29; or
 (b) a heavy chain variable region comprising an amino acid sequence represented by SEQ ID NO: 24, a light chain variable region comprising an amino acid sequence represented by SEQ ID NO:28, a heavy chain constant region comprising an amino acid sequence represented by SEQ ID NO:32 and a light chain constant region comprising an amino acid sequence represented by SEQ ID NO:34.

8. The isolated antibody or the antigen-binding portion thereof of claim 2, which (a) does not bind to TIM-1; (b) does not bind to TIM-4; (c) inhibits binding of TIM-3 to galectin-9; inhibits binding of TIM-3 to phosphatidylserine; (d) induces pre-stimulated T cell to release IL-2; (f) does not induce ADCC on TIM-3-expressing cells; and/or (g) does not induce CDC on TIM-3-expressing cells.

9. The isolated antibody or the antigen-binding portion thereof of claim 2, which is a human or chimeric antibody.

10. The isolated antibody or the antigen-binding portion thereof of claim 2, which is monoclonal or bispecific.

11. The isolated antibody or the antigen-binding portion thereof of claim 2, wherein the antigen-binding portion is selected from (i) a Fab fragment; (ii) a F(ab')$_2$ fragment; and (iii) a Fv fragment.

12. A pharmaceutical composition comprising the antibody or the antigen-binding portion thereof of claim 2, and a pharmaceutically acceptable carrier.

13. The pharmaceutical composition of claim 12, further comprising at least one additional anti-cancer antibody, a cytokine, a costimulatory antibody or a chemotherapeutic agent.

14. A method for inhibiting tumor growth or for enhancing an immune response in a subject, comprising administering to the subject a therapeutically effective amount of the pharmaceutical composition of claim 12.

15. The method of claim 14, wherein the tumor is B cell lymphoma, chronic lymphocytic leukemia, multiple myeloma, melanoma, colon adenocarcinoma, pancreas cancer, colon cancer, gastric intestine cancer, prostate cancer, bladder cancer, kidney cancer, ovary cancer, cervix cancer, breast cancer, lung cancer, or nasopharynx cancer.

16. The method of claim 14, wherein at least one additional anti-cancer antibody or a cytokine or a costimulatory antibody or a chemotherapeutic agent is administered with the pharmaceutical composition.

17. The method of claim 16, wherein the anti-cancer antibody is an anti-VISTA antibody, an anti-PD-1 antibody, an anti-PD-L1 antibody, an anti-LAG-3 antibody and/or an anti-CTLA-4 antibody.

18. The method of claim 16, wherein the cytokine is IL-2 and/or IL-21.

19. The method of claim 16, wherein the costimulatory antibody is an anti-CD137 and/or anti-GITR antibody.

20. The method of claim 16, wherein the chemotherapeutic agent is a cytotoxic agent.

21. A nucleic acid molecule encoding the antibody or the antigen-binding portion thereof of claim 2.

22. An expression vector comprising the nucleic acid molecule of claim 21.

23. A host cell comprising the nucleic acid molecule of claim 21.

* * * * *